United States Patent
Castellano

(10) Patent No.: US 6,447,475 B1
(45) Date of Patent: Sep. 10, 2002

(54) GAS POWER SOURCES FOR A NEEDLE-LESS INJECTOR AND NEEDLE-LESS INJECTORS INCORPORATING THE SAME

(75) Inventor: Thomas P. Castellano, Los Angeles, CA (US)

(73) Assignee: Pen Jet Corporation, Los Angeles, CA (US)

( * ) Notice: Subject to any disclaimer, the term of this patent is extended or adjusted under 35 U.S.C. 154(b) by 0 days.

(21) Appl. No.: 09/566,928

(22) Filed: May 6, 2000

Related U.S. Application Data

(63) Continuation of application No. 09/215,769, filed on Dec. 19, 1998, now Pat. No. 6,063,053, which is a continuation of application No. 08/727,911, filed on Oct. 9, 1996, now Pat. No. 5,851,198, which is a continuation-in-part of application No. 08/719,459, filed on Sep. 25, 1996, now Pat. No. 5,730,723, which is a continuation-in-part of application No. 08/541,470, filed on Oct. 10, 1995, now abandoned, application No. 09/566,928, which is a continuation of application No. 09/192,079, filed on Nov. 14, 1998.

(51) Int. Cl.7 ................................................ A61M 5/30
(52) U.S. Cl. ........................................................ 604/68
(58) Field of Search ............................ 604/68, 70, 131, 604/134, 135, 136, 137

(56) References Cited

U.S. PATENT DOCUMENTS

| | | |
|---|---|---|
| 4,913,699 A | 4/1990 | Parsons |
| 5,009,637 A | 4/1991 | Newman et al. |
| 5,730,723 A | 3/1998 | Castellano et al. |
| 5,851,198 A | 12/1998 | Castellano et al. |
| 6,063,053 A | 5/2000 | Castellano et al. |
| 6,080,130 A | 6/2000 | Castellano |

Primary Examiner—Manuel Mendez
(74) Attorney, Agent, or Firm—Pillsbury Winthrop LLP

(57) ABSTRACT

A needle-less injector suitable for injecting fluid through a skin surface of a patient includes a housing, a driver, an intruding gas chamber activating mechanism and a trigger. The housing containing the fluid and a sealed gas storage chamber containing a gas. The driver forces the fluid out of the housing at a sufficient speed to pierce the skin surface of the patient. The intruding gas chamber activating mechanism is mounted in the housing to intrude through the sealed gas chamber to release gas seal into the housing. The trigger is operatively coupled to the intruding gas chamber activating mechanism to release the gas from the gas chamber into the housing to activate the driver to force the fluid out of the housing. The trigger is activated by moving the trigger towards and orifice in the housing and/or upon application of a predetermined amount of pressure to the trigger that is opposed by a predetermined amount of resistance from the skin surface of the patient. The predetermined amount of resistance results from the housing having contact with the skin surface of the patient, and when this predetermined amount of resistance is reached the liquid medication is forced out of the housing by the driver to pierce the skin surface of the patient. In particular variations, the intruding gas chamber activating mechanism includes a valve member that is displaced and intrudes into the sealed gas chamber to release the gas from the gas chamber.

30 Claims, 32 Drawing Sheets

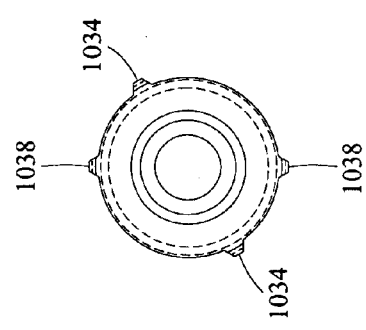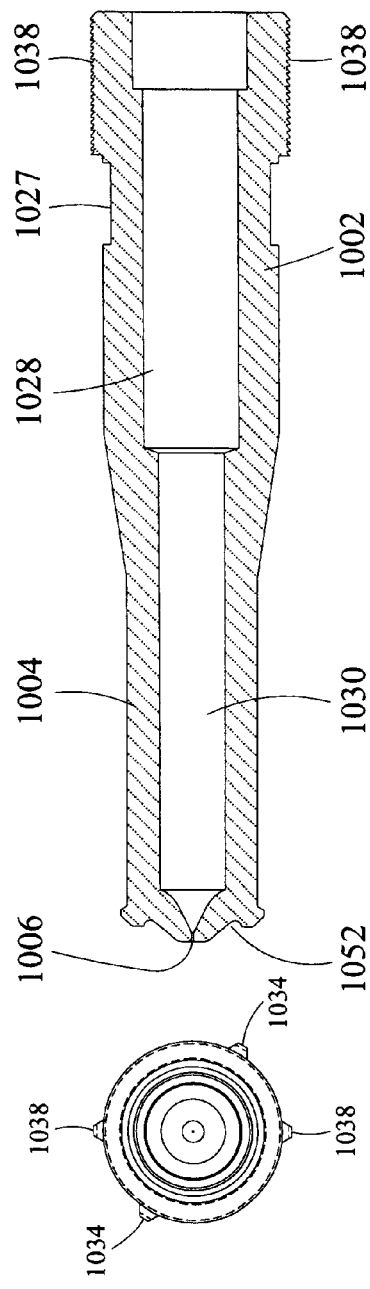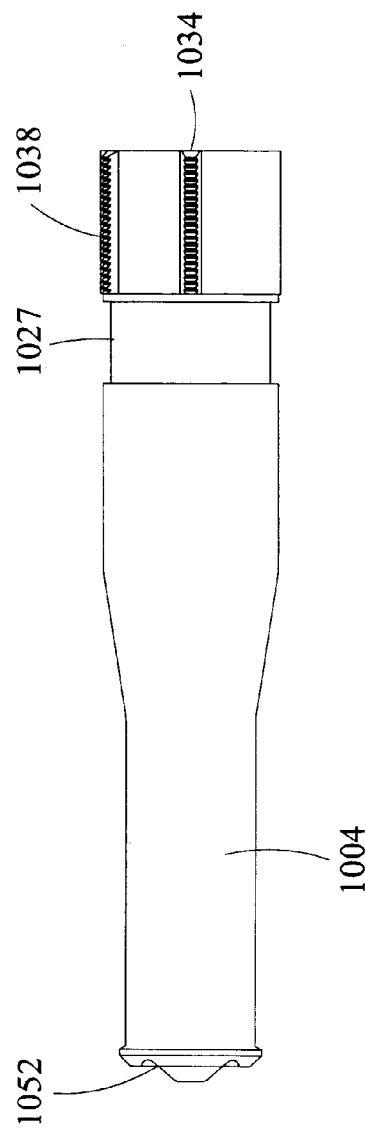

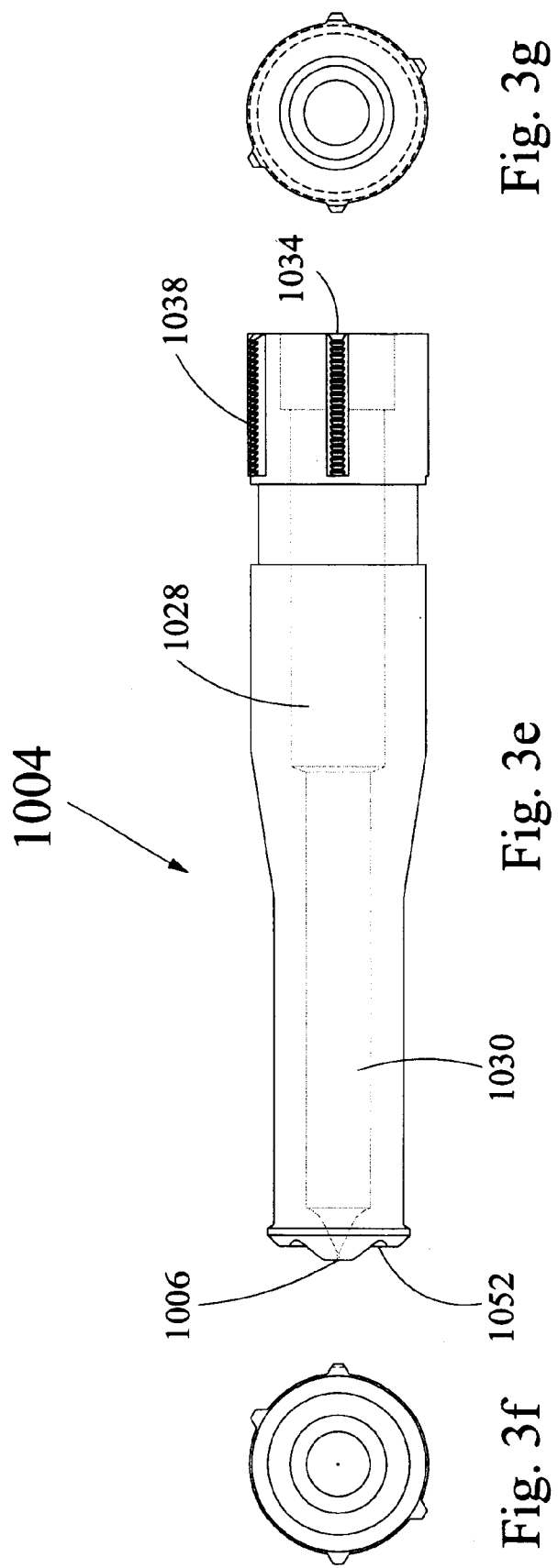

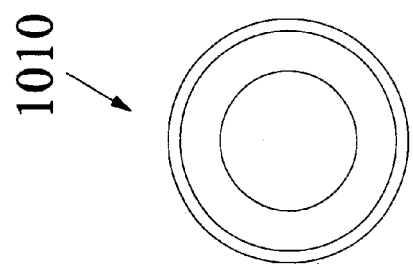
Fig. 4a
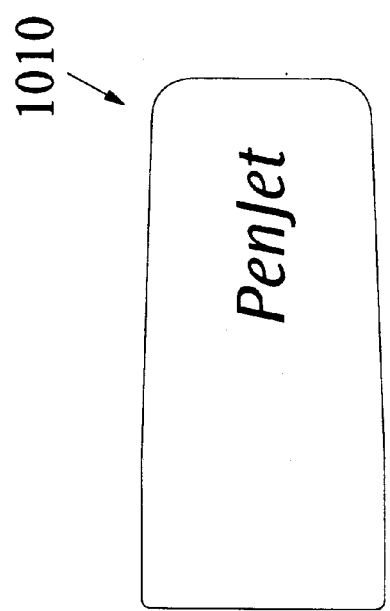
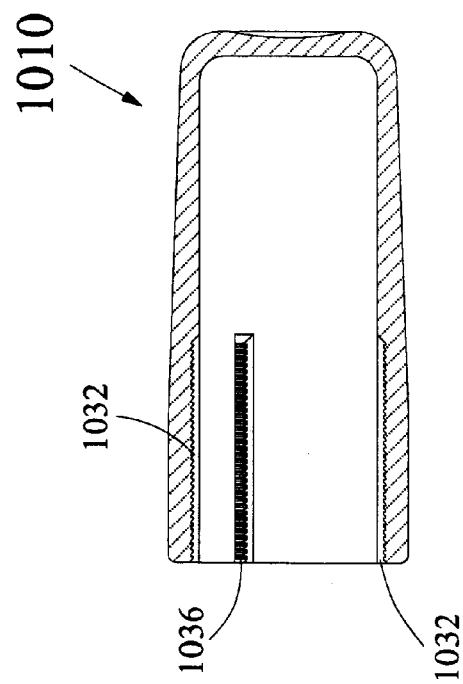
Fig. 4b
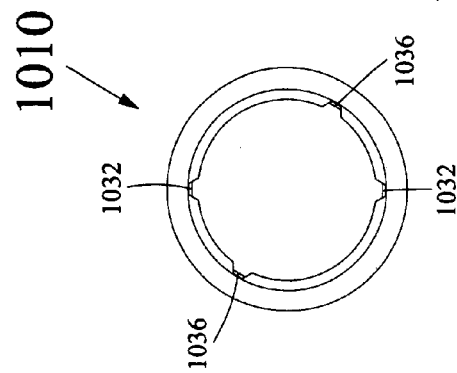
Fig. 4c
Fig. 4d

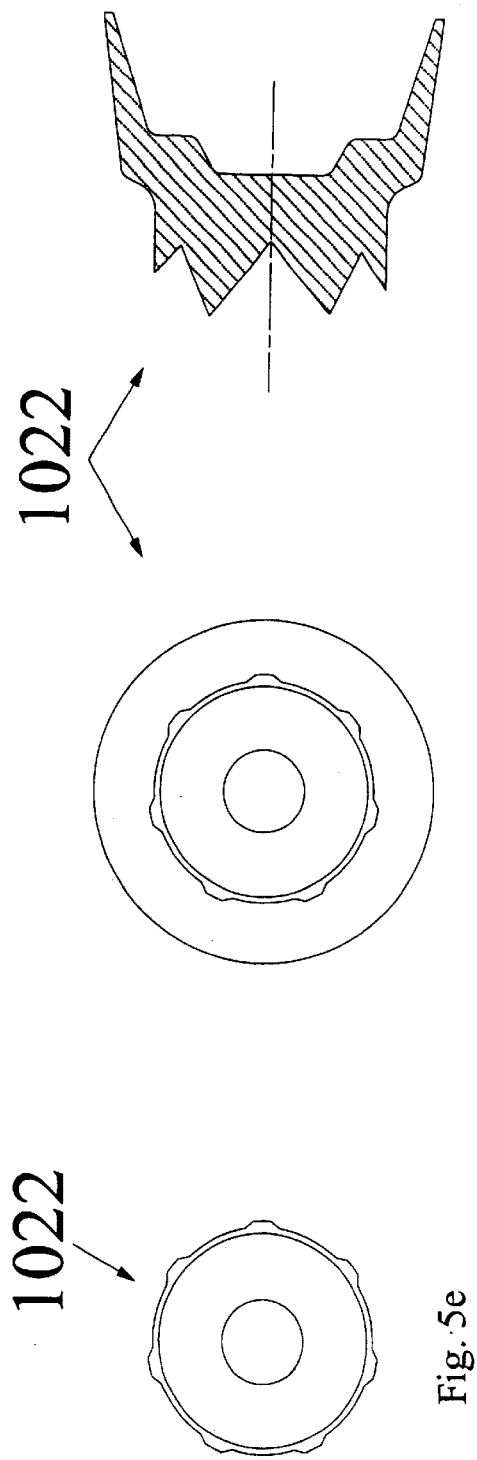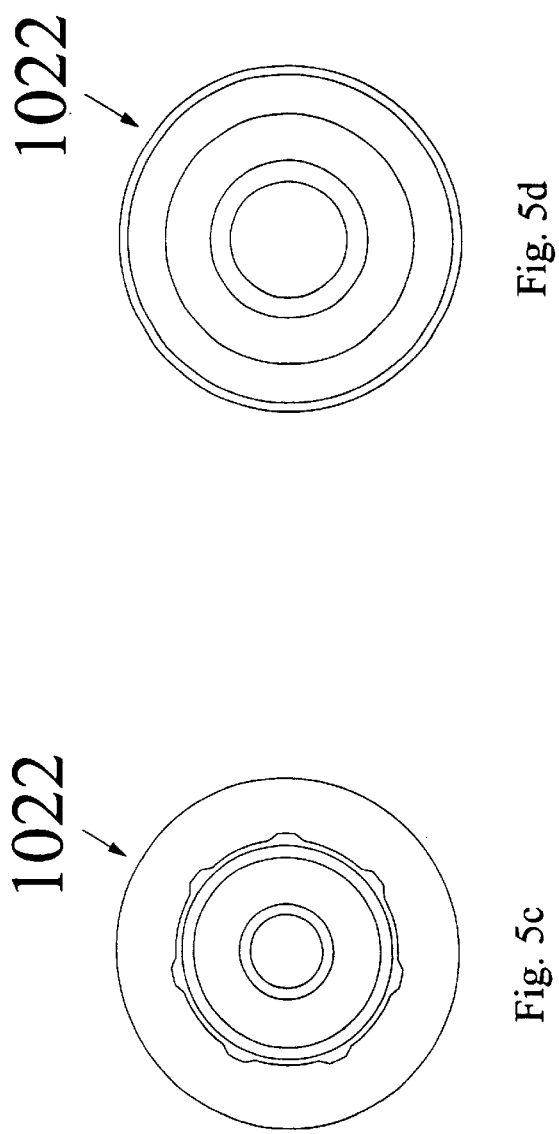

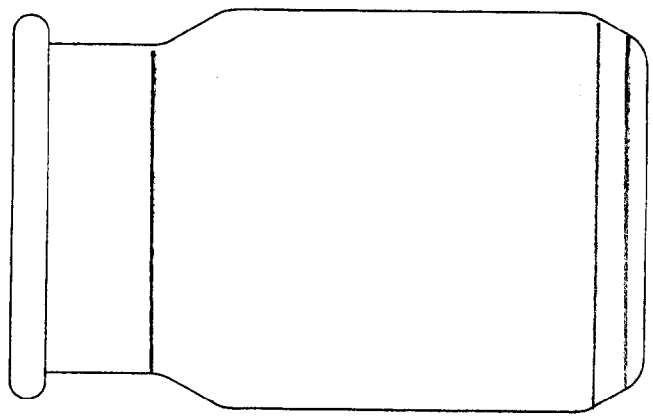
Fig. 7a
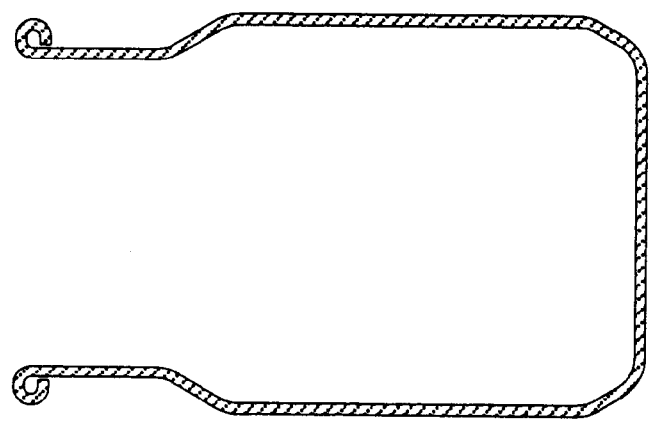
Fig. 7b

1026

1026

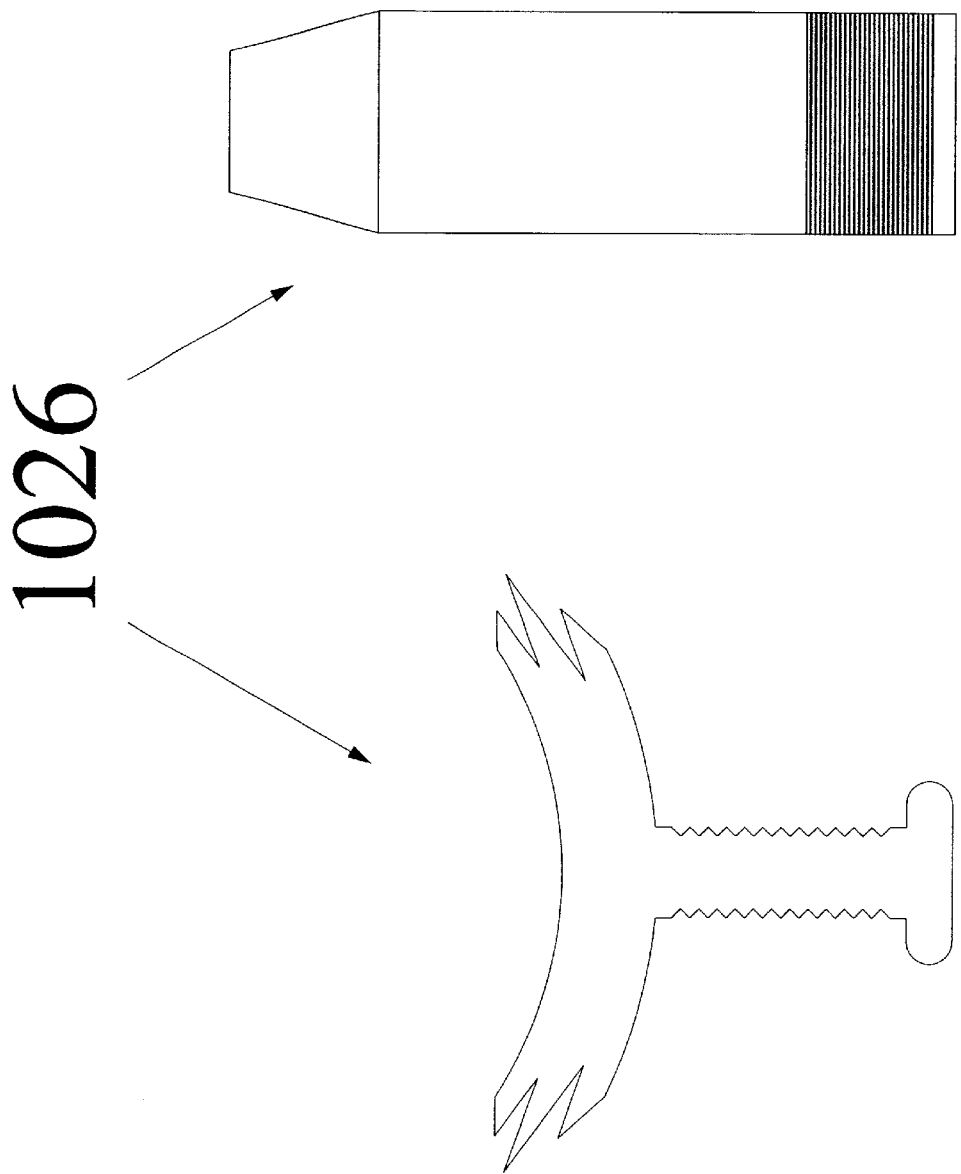

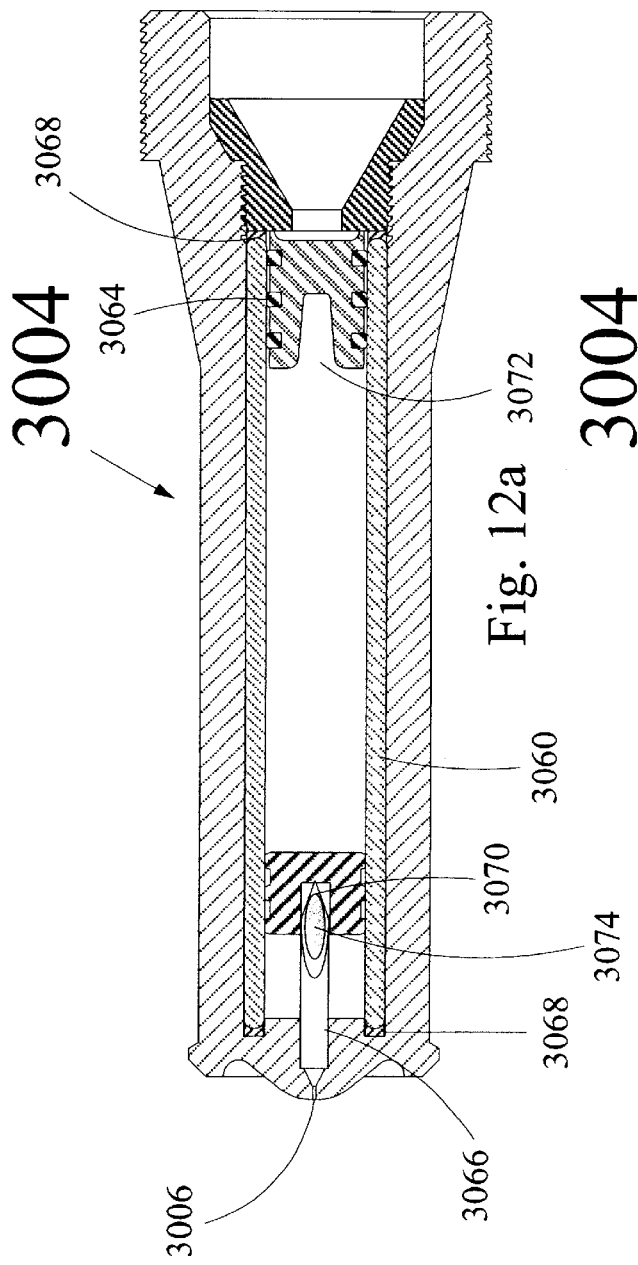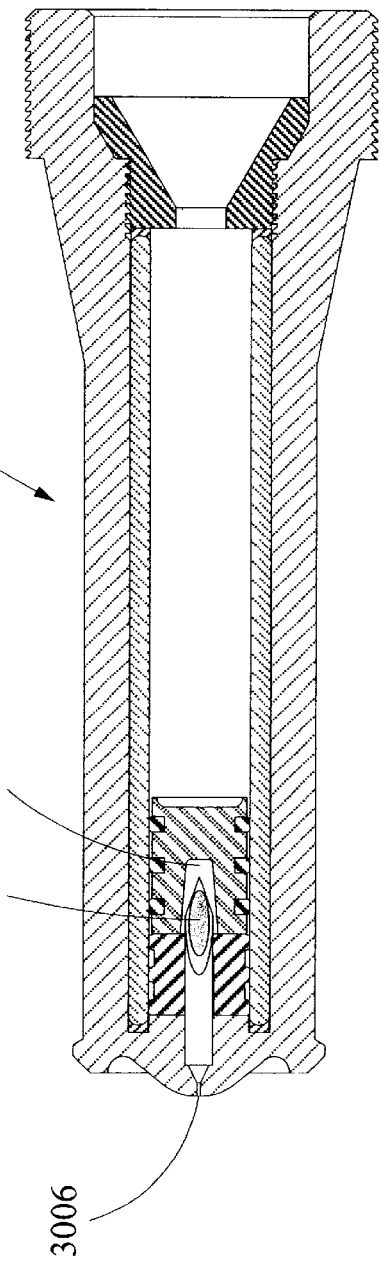
Fig. 12a
Fig. 12b

5012

5012

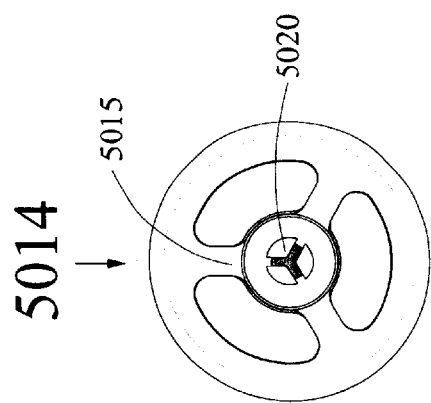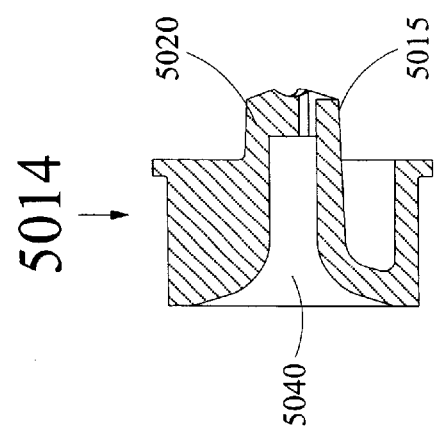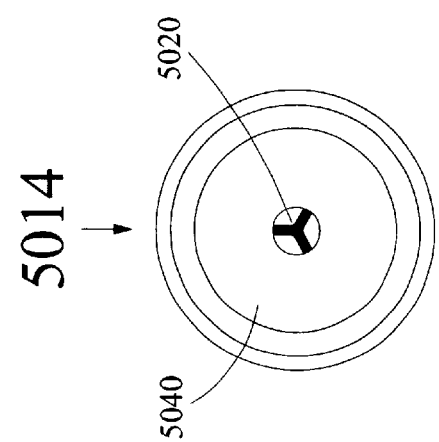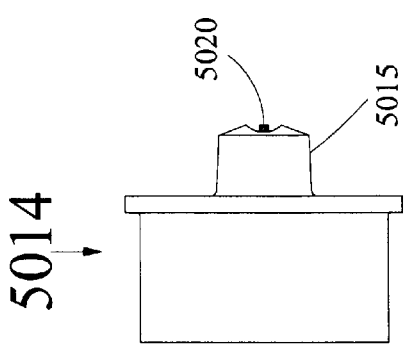

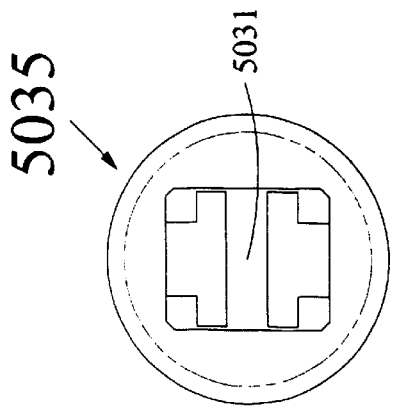
Fig. 25d
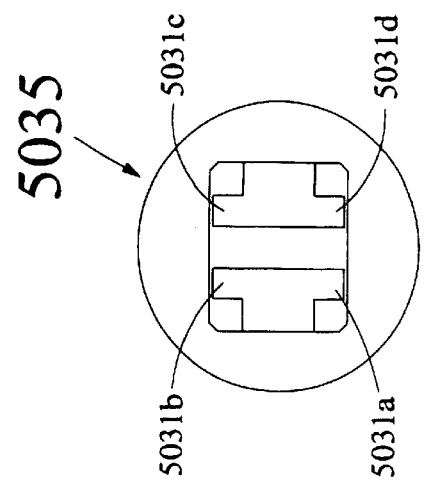
Fig. 25f
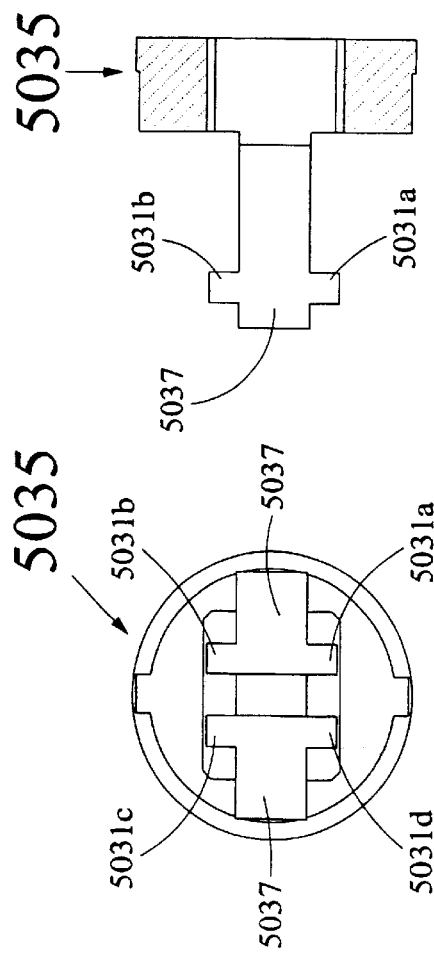
Fig. 25b
Fig. 25a
Fig. 25c
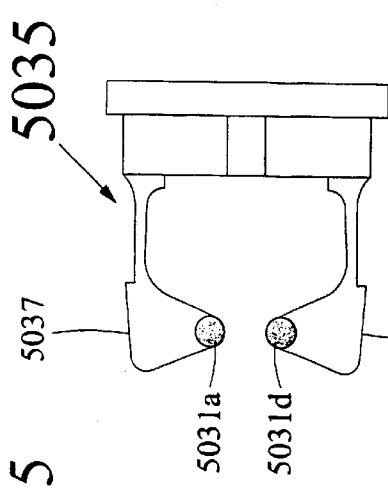
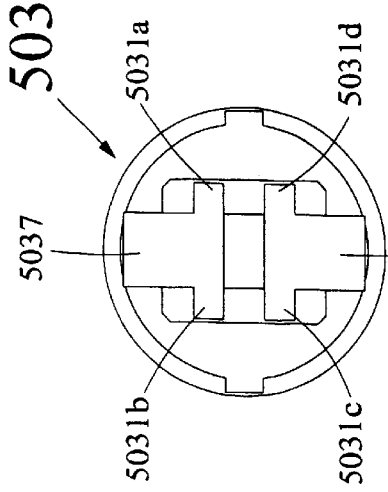
Fig. 25e

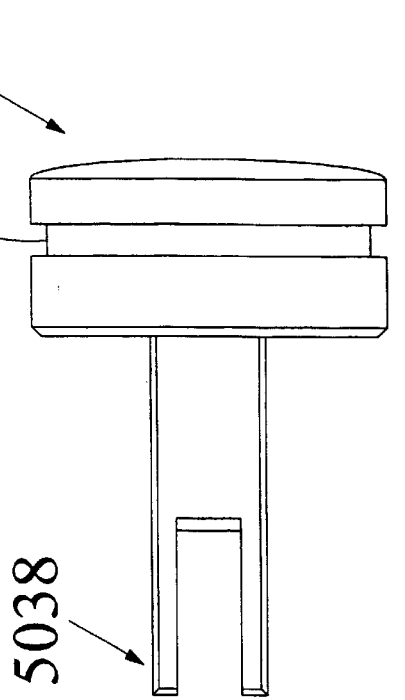
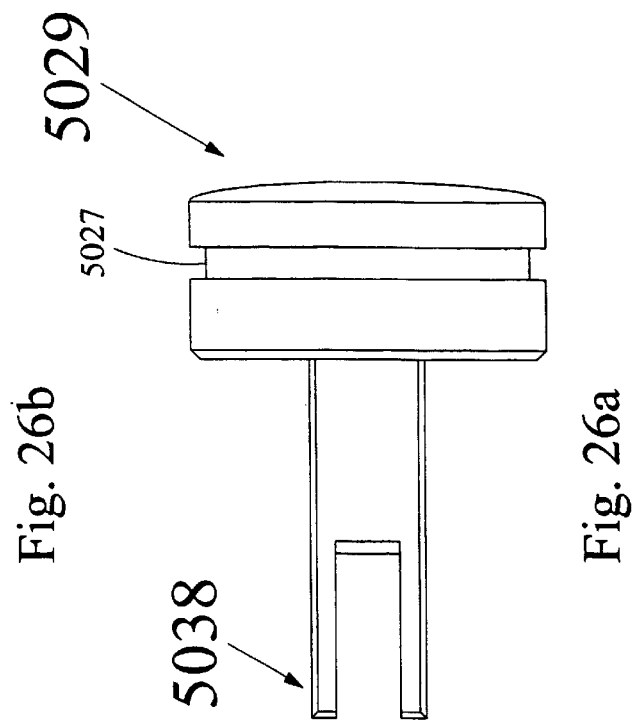
Fig. 26a
Fig. 26b
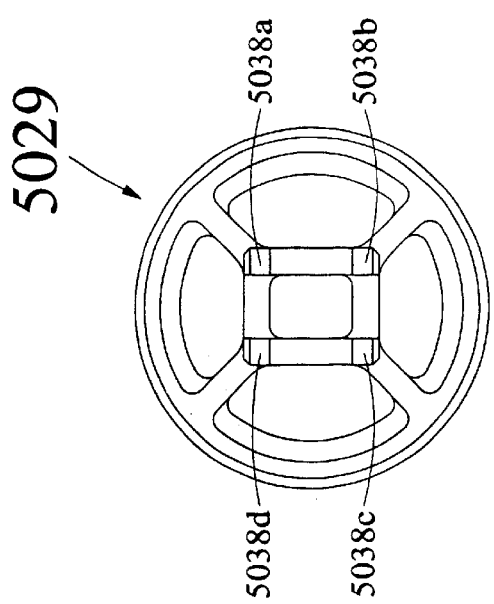
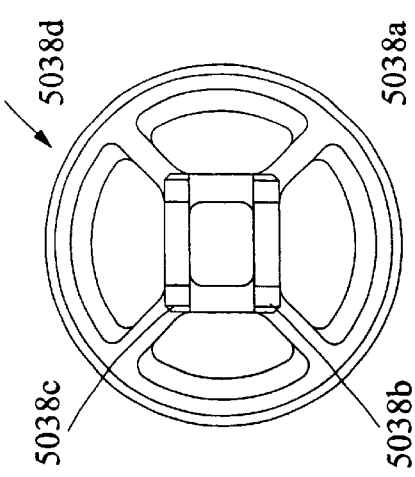
Fig. 26d
Fig. 26c

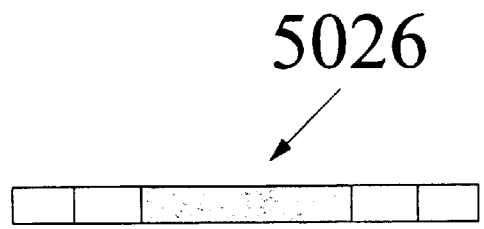
Fig. 28d
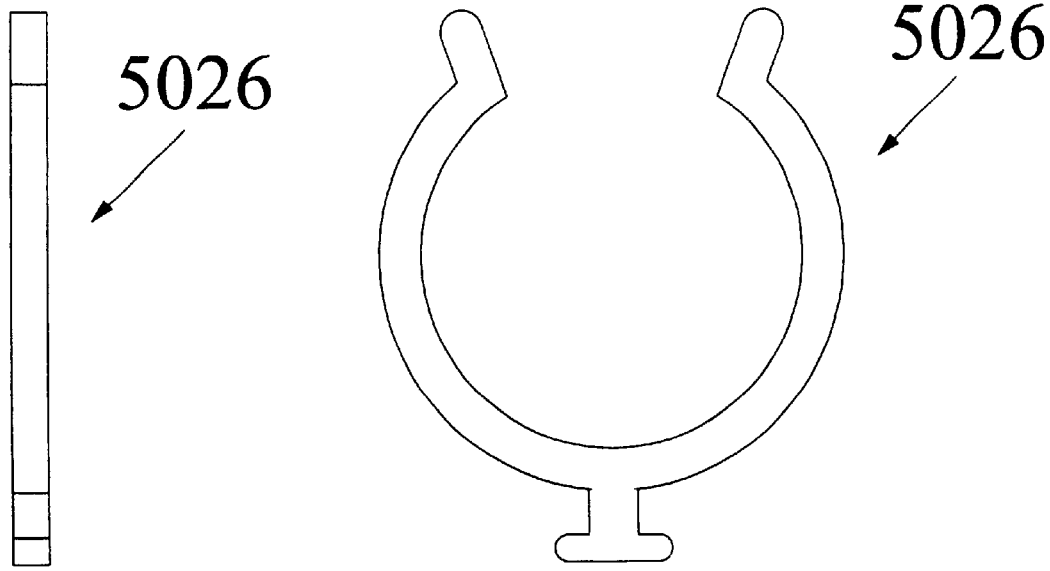
Fig. 28b
Fig. 28a
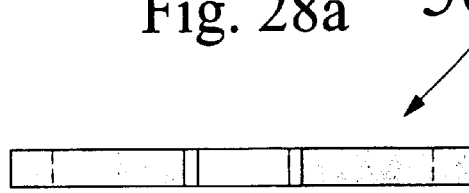
Fig. 28c

GAS POWER SOURCES FOR A NEEDLE-LESS INJECTOR AND NEEDLE-LESS INJECTORS INCORPORATING THE SAME

RELATED APPLICATIONS

This application is a continuation of U.S. patent application Ser. No. 09/215,769 filed Dec. 19, 1998, now U.S. Pat. No. 6,063,053, which is a continuation of U.S. patent application Ser. No. 08/727,911 filed Oct. 9, 1996, now U.S. Pat. No. 5,851,198, which is a continuation-in-part of U.S. patent application Ser. No. 08/719,459 filed Sep. 25, 1996, now U.S. Pat. No. 5,730,723, which is a continuation-in-part of U.S. patent application Ser. No. 08/541,470 filed Oct. 10, 1995, now abandoned; and is a continuation to U.S. patent application Ser. No. 09/192,079 filed Nov. 14, 1998, now U.S. Pat. No. 6,080,130, all of which are hereby incorporated by reference in their entirety.

FIELD OF THE INVENTION

This invention relates to improved gas power sources for a needle-less injector, and in particular, embodiments for providing gas power to a needle-less injector and needleless injectors with greater reliability and at reduced manufacturing cost.

BACKGROUND OF THE INVENTION

Typically, needle-less medication injections are performed with "permanent gun" instruments, generally referred to as "jet injectors". These devices use either a compression spring or a compressed inert gas to propel the fluid medication (via a push rod plunger) through a small orifice (an injector nozzle) which rests perpendicular to and against the injection site. The fluid medication is generally accelerated at a high rate to a speed of between about 800 feet per second (fps) and 1,200 fps (approximately 244 and 366 meters per second, respectively). This causes the fluid to pierce through the skin surface without the use of a needle, resulting in the medication being deposited in a flower pattern under the skin surface. This method of medication delivery is referred to as a subcutaneous injection.

Conventional, reusable jet injectors are cumbersome and awkward to use. Preparing a typical, reusable jet injector for administering an injection requires several steps. For example, prior to each injection, the injector nozzle must be sterilized. The operator removes the delivery nozzle from the jet injector and boils the nozzle in water to assure a reasonable degree of sterilization. After the nozzle is cleaned, the user replaces it on the instrument and prepares the instrument for loading the medication which is to be injected into the skin. A concern often associated with the nozzle in these reusable systems is that, due to a relatively small opening (approximately 0.004" or less), the nozzle has a tendency to clog up if the device is left unused for a period of time or if the user does not clean the instrument each time after being used and prior to its reuse.

In addition, loading known reusable jet injectors with medication is a time consuming and delicate operation. First, an adapter which contains a needle is placed through the rubber septum of the medication vial. The nozzle of the jet injector is then mated to the needle adapter in the medication vial. The operator then proceeds to draw up medication into the delivery chamber of the jet injector. This operation may be repeated several times, until the trapped air in the delivery chamber is removed. When this pre-injection operation is complete, the operator selects an injection site and administers the injection.

However, a used and worn delivery orifice can slow down the delivery speed of the injected fluid, which results in inadequate penetration and causes bruising of the skin at the injection site. In addition, the improper use of jet injectors creates bruising (subdermal hematoma) when the nozzle is not firmly pressed against the injection site. Bruising also may occur if the nozzle opening (orifice) is partially clogged or worn out.

Conventional jet injectors are also somewhat dangerous to use, since they can be discharged without being placed against the skin surface. With a fluid delivery speed of about 800 fps or higher, a jet injector could injure a person's eye at a distance of up to 15 feet. It should also be noted that jet injectors which have not been properly sterilized are notorious for creating infections at the injection site. In addition, if a jet injector is not positioned properly against the injection site, the injection can be short of the measured dosage, thereby creating wetting on the skin surface, which leads to additional problems associated with improper dosage amounts.

Moreover, it should also be noted that compression spring propelled jet injectors do not offer linear delivery speeds (constant speed of the fluid being injected). In addition to this problem, spring propelled jet injectors with weak (e.g., deteriorated) springs often slow the fluid delivery speed down while the fluid is being administered into the skin which can result in improper fluid penetration. Reduced speed of the fluid can cause improper dosing and bruising at the injection site (referred to as subdermal hematoma).

In addition, if the inert gas is not quickly and properly expelled, the medication may be improperly administered like the springs. Conventional disposable needle-less injectors, such as those shown in U.S. Pat. No. 4,913,699 to Parsons and U.S. Pat. No. 5,009,637 to Newman et al. show a breakable tube that is shattered or cracked open by a side mounted trigger. Difficulties arise in the need to maintain tight tolerances on the breakable member, since minor changes in thickness can dramatically effect the pressure needed to deploy the gas from the gas chamber of the device. In addition, the broken shards of the breakable member are ejected at high speed when the gas is expelled and these shards can occasionally jam in between the plunger driver and the housing, thereby preventing proper operation of the needle-less injector. Attempts to prevent small shards from being formed would obviate some of this potential, but tend to make activation of the device more difficult.

SUMMARY OF THE DISCLOSURE

It is an object of an embodiment of the present invention to provide improved gas power sources for a needle-less injector, syringe or the like, that obviate for practical purposes, the above-mentioned limitations.

According to an embodiment of the present invention, a needle-less injector suitable for injecting fluid through a skin surface of a patient includes a housing, a driver, an intruding gas chamber activating mechanism and a trigger. The housing containing the fluid and a sealed gas storage chamber containing a gas. The driver forces the fluid out of the housing at a sufficient speed to pierce the skin surface of the patient. The intruding gas chamber activating mechanism is mounted in the housing to intrude through the sealed gas chamber to release gas seal into the housing. The resistance sensitive trigger is operatively coupled to the intruding gas chamber activating mechanism to release the gas from the gas chamber into the housing to activate the driver to force the fluid out of the housing. The resistance sensitive trigger is activated upon application of a predetermined amount of pressure to the resistance sensitive trigger that is opposed by a predetermined amount of resistance from the skin surface of the patient. The predetermined amount of resistance results from the housing having contact with the skin surface of the patient, and when this predetermined amount of resistance is reached the fluid is forced out of the housing by the driver to pierce the skin surface of the patient. In particular embodiments, the intruding gas chamber activating mechanism includes a valve member that is displaced and intrudes into the sealed gas chamber to release the gas from the gas chamber.

In farther embodiments, the housing of the needle-less injector includes a face that is adapted to align the housing to produce the predetermined amount of resistance to allow for activation of the resistance sensitive trigger. Also, the resistance sensitive trigger is preferably coupled to the housing to permit axial movement of the resistance sensitive trigger along the housing. However, the fit tolerances between the housing and the resistance sensitive trigger are selected to permit activation of the resistance sensitive trigger when the housing is aligned between 0 and 10 degrees off an axis perpendicular to the skin surface of the patient. In addition, the resistance sensitive trigger is preferably positioned to be between the skin surface of the patient and an activating appendage (such as an hand, arm or the like) of a user when activating the driver to force the fluid out from the housing.

In particular embodiments, the resistance sensitive trigger includes a resistance element that activates at a lower amount of pressure than the predetermined amount of resistance by the skin surface of the patient. For example, the resistance sensitive trigger includes a cap that is slidably attached to the housing and the resistance element includes a spring coupled between the housing and the cap. Thus, upon application of the predetermined amount of pressure to the cap of the resistance sensitive trigger, the spring compresses when the opposing resistance from the skin surface of the patient reaches the predetermined amount of resistance to activate the driver to force the fluid out of the housing to pierce the skin surface of the patient.

In additional embodiments, the housing containing the fluid includes a glass insert, a septum seal and a plunger septum to form a fluid chamber. The septum seal and the plunger septum are moved by the drive mechanism to force the fluid out of the fluid chamber. In particular embodiments, the housing further includes finger rests to support the housing as the resistance sensitive trigger activates the driver.

In further embodiments of the present invention, a needle-less injector suitable for injecting fluid through a skin surface of a patient includes a housing, a driver, a gas chamber penetrating mechanism and a trigger. The housing containing the fluid and a sealed gas storage chamber containing a gas. The driver forces the fluid out of the housing at a sufficient speed to pierce the skin surface of the patient. The gas chamber penetrating mechanism is mounted in the housing to intrude through the sealed gas chamber to release gas seal into the housing. The resistance sensitive trigger is operatively coupled to the gas chamber penetrating mechanism to release the gas from the gas chamber into the housing to activate the driver to force the fluid out of the housing. The resistance sensitive trigger is activated upon application of a predetermined amount of pressure to the resistance sensitive trigger that is opposed by a predetermined amount of resistance from the skin surface of the patient. The predetermined amount of resistance results from the housing having contact with the skin surface of the patient, and when this predetermined amount of resistance is reached the fluid is forced out of the housing by the driver to pierce the skin surface of the patient. In particular embodiments, the gas chamber penetrating mechanism includes a valve member that is displaced and penetrates the sealed gas chamber to release the gas from the gas chamber. In other embodiments, the gas chamber penetrating mechanism includes a piercing ember that penetrates the gas chamber to pierce a diaphragm in the gas chamber to release the gas from the sealed gas chamber into the housing.

In additional embodiments, the housing containing the fluid includes a glass insert, a septum seal and a plunger septum to form a fluid chamber. The septum seal and the plunger septum are moved by the drive mechanism to force the fluid out of the fluid chamber. In particular embodiments, the housing further includes finger rests to support the housing as the resistance sensitive trigger activates the driver.

According to another embodiment of the present invention, a needle-less injector suitable for injecting fluid through a skin surface of a patient includes a housing, a driver, an intruding gas chamber activating mechanism and a trigger. The housing containing the fluid, a sealed gas storage chamber containing a gas, and an orifice. The driver forces the fluid out of the orifice of the housing at a sufficient speed to pierce the skin surface of the patient. The intruding gas chamber activating mechanism is mounted in the housing to intrude through the sealed gas chamber to release gas seal into the housing. The trigger is operatively coupled to the intruding gas chamber activating mechanism to release the gas from the gas chamber into the housing to activate the driver to force the fluid out of the orifice of the housing by moving the trigger towards the orifice so that the fluid is forced out of the housing by the driver to pierce the skin surface of the patient. In particular embodiments, the intruding gas chamber activating mechanism includes a valve member that is displaced and intrudes into the sealed gas chamber to release the gas from the gas chamber.

In further embodiments, the housing of the needle-less injector includes a face that is adapted to align the housing to produce the predetermined amount of resistance to allow for activation of the trigger. Also, the trigger is preferably coupled to the housing to permit axial movement of the trigger along the housing. However, the fit tolerances between the housing and the trigger are selected to permit activation of the trigger when the housing is aligned between 0 and 10 degrees off an axis perpendicular to the skin surface of the patient. In addition, the trigger is preferably positioned to be between the skin surface of the patient and an activating appendage (such as an hand, arm or the like) of a user when activating the driver the force to fluid out from the housing.

In particular embodiments, the trigger is activated upon application of a predetermined amount of pressure to the trigger that is opposed by a predetermined amount of resistance from the skin surface of the patient. The predetermined amount of resistance results from the housing having contact with the skin surface of the patient, and when this predetermined amount of resistance is reached the fluid is forced out of the housing by the driver to pierce the skin surface of the patient. In particular embodiments, the trigger includes a resistance element that activates at a lower amount of pressure than the predetermined amount of resistance by the skin surface of the patient. For example, the trigger includes at least one actuator that is slidably attached to the housing and the resistance element includes a spring coupled between the housing and the at least one actuator. Thus, upon application of the predetermined amount of pressure to the at least one actuator of the trigger, the spring compresses when the opposing resistance from the skin surface of the patient reaches the predetermined amount of resistance to activate the driver to force the fluid out of the housing to pierce the skin surface of the patient.

In additional embodiments, the housing containing the fluid includes a glass insert, a septum seal and a plunger septum to form a fluid chamber. The septum seal and the plunger septum are moved by the drive mechanism to force the fluid out of the fluid chamber. In particular embodiments, the housing further includes finger rests to support the housing as the trigger activates the driver.

In still further embodiments of the present invention, a needle-less injector suitable for injecting fluid through a skin surface of a patient includes a housing, a driver, a gas chamber penetrating mechanism and a trigger. The housing containing the fluid and a sealed gas storage chamber containing a gas. The driver forces the fluid out of the housing at a sufficient speed to pierce the skin surface of the patient. The gas chamber penetrating mechanism is mounted in the housing to intrude through the sealed gas chamber to release gas seal into the housing. The trigger is operatively coupled to the gas chamber penetrating mechanism to release the gas from the gas chamber into the housing to activate the driver to force the fluid out of the orifice of the housing by moving the trigger towards the orifice so that the fluid is forced out of the housing by the driver to pierce the skin surface of the patient. In other embodiments, the trigger is activated upon application of a predetermined amount of pressure to the trigger that is opposed by a predetermined amount of resistance from the skin surface of the patient. The predetermined amount of resistance results from the housing having contact with the skin surface of the patient, and when this predetermined amount of resistance is reached the fluid is forced out of the housing by the driver to pierce the skin surface of the patient. In particular embodiments, the gas chamber penetrating mechanism includes a valve member that is displaced and penetrates the sealed gas chamber to release the gas from the gas chamber. In other embodiments, the gas chamber penetrating mechanism includes a piercing member that penetrates the gas chamber to pierce a diaphragm in the gas chamber to release the gas from the sealed gas chamber into the housing.

In additional embodiments, the housing containing the fluid includes a glass insert, a septum seal and a plunger septum to form a fluid chamber. The septum seal and the plunger septum are moved by the drive mechanism to force the fluid out of the fluid chamber. In particular embodiments, the housing further includes finger rests to support the housing as the resistance sensitive trigger activates the driver.

In still another embodiment of the present invention, a needle-less injector suitable for injecting a fluid through skin of a patient includes a housing, a driver and an at least partially resistance sensitive trigger. The housing contains the fluid, and includes an injection end with an orifice and a trigger portion opposite the injection end. The injection end of the housing is stationary and fixed relative to the housing. The housing also includes finger rests. The driver forces the fluid out of the orifice of the injection end of the housing at a sufficient speed to deliver the fluid to the skin of the patient. The at least partially resistance sensitive trigger is operatively coupled to the driver and the trigger portion of the housing. The movement of the partially resistance sensitive trigger activates the driver to force the fluid out of the orifice of the injection end of the housing. Upon application of a predetermined amount of pressure to the partially resistance sensitive trigger to move the partially resistance sensitive trigger relative to the housing towards the injection end and the skin and that is opposed by a predetermined amount of resistance from the skin of the patient resulting from the injection end of the housing having contact with the skin of the patient and resistance from the finger stops, the forced out fluid will be delivered to the skin of the patient. In particular embodiments, the partially resistance sensitive trigger moves closer towards the skin during an injection while the injection end and the housing remain substantially stationary relative to the skin, and the partially resistance sensitive trigger is operatively decoupled from the driver after the injection.

In further embodiments, the housing includes a face on the housing for contacting the skin of the patient and align an orientation of the housing to produce the predetermined amount of resistance to allow for activation of the partially resistance sensitive trigger. In particular embodiments, the partially resistance sensitive trigger is coupled to the housing to permit axial movement of the partially resistance sensitive trigger along the housing, wherein relative sizes of the housing and the partially resistance sensitive trigger permit activation of the partially resistance sensitive trigger when the housing is aligned between 0 and 15 degrees off an axis perpendicular to the skin of the patient. Also, the partially resistance sensitive trigger can be positioned to be between the skin of the patient and an activating appendage of a user when activating the driver to force the fluid out of the housing. In other embodiments, the partially resistance sensitive trigger includes a resistance element that activates at a lower amount of pressure than the predetermined amount of resistance by the skin of the patient. Preferably, the partially resistance sensitive trigger includes an actuator slidably attached to the housing and the resistance element includes a spring coupled between the housing and the actuator. Upon application of the predetermined amount of pressure to the cap of the partially resistance sensitive trigger the spring compresses, when the opposing resistance from the skin of the patient reaches the predetermined amount of resistance, to activate the driver to force the fluid out of the housing to penetrate the skin of the patient. In addition, the needle-less injector is compressed gas activated.

In yet another embodiment of the present invention an ampoule for use with a needle-less injector suitable for injecting fluid through skin of a patient includes a housing, a glass insert, a septum seal and a plunger septum. The housing formed from a non-glass material, and the housing forms an internal chamber. The glass insert has two ends and is contained within the internal chamber of the housing. The moveable septum seal closes off one end of the glass insert, and the moveable plunger septum closes off the other end of the glass insert to form a fluid chamber. In particular embodiments, the housing further includes an orifice, and the moveable septum seal provides a pathway for the fluid to exit the medication chamber through the orifice in the housing. In further embodiments, the housing further includes a piercing element that pierces the septum seal to form the pathway for the fluid to exit the orifice of the housing.

Other features and advantages of the invention will become apparent from the following detailed description, taken in conjunction with the accompanying drawings which illustrate, by way of example, various features of embodiments of the invention.

BRIEF DESCRIPTION OF THE DRAWINGS

A detailed description of embodiments of the invention will be made with reference to the accompanying drawings, wherein like numerals designate corresponding parts in the several figures.

FIGS. 3a–3g are various views of an ampoule and plunger housing in accordance with the first embodiment of the present invention. FIG. 3a is a side perspective view, FIG. 3b is a side cross-sectional view, FIG. 3c is a first end view, FIG. 3d is a second end view, FIG. 3e is a side plan view, FIG. 3f is a first end plan view, and FIG. 3g is a second end plan view.

FIGS. 4a–d are various view of the actuator cap in accordance with the first embodiment of the present invention. FIG. 4a is a side perspective view, FIG. 4b is a side cross-sectional view, FIG. 4c is a first end view, and FIG. 4d is a second end view.

FIGS. 5a–g are various view of the plunger shaft in accordance with the first embodiment of the present invention. FIG. 5a is a side perspective view, FIG. 5b is a side cross-sectional view, FIG. 5c is a first end view, FIG. 5d is a second end view, FIG. 5e is a first enlarged cross-sectional view as shown along the line B–BB in FIG. 5a, FIG. 5f is a second enlarged cross-sectional view as shown along the line A–AA in FIG. 5a, and FIG. 5g is an enlarged partial side cross-sectional view a plunger cap end.

FIG. 6a is a side perspective view, FIG. 6b is a side cross-sectional view, FIG. 6c is a first end view, and FIG. 6d is a second end view.

FIGS. 7a–b are various view of the gas capsule in accordance with the first embodiment of the present invention. FIG. 7a is a side perspective view, and FIG. 7b is a side cross-sectional view.

FIG. 8a is a side perspective view, FIG. 8b is a side cross-sectional view, FIG. 8c is a first end view, and FIG. 8d is a second end view.

FIGS. 9a–e are various view of the safety clamp in accordance with the first embodiment of the present invention. FIG. 9a is a top plan view, FIG. 9b is a side perspective view, FIG. 9c is a first end view, FIG. 9d is a second end view, and FIG. 9e is an enlarged partial plan view of the handle of the safety clamp.

FIGS. 12a and b are side perspective views of an ampoule in accordance with a third embodiment of the present invention.

FIG. 13a is a side perspective view and FIG. 13b is an end view.

FIG. 17a is a side perspective view, FIG. 17b is a side cross-sectional view, FIG. 17c is a first end view, and FIG. 17d is a second end view.

FIG. 18a is a side perspective view, FIG. 18b is a side cross-sectional view, FIG. 18c is a first end view, and FIG. 18d is a second end view.

FIG. 19a is a side perspective view, FIG. 19b is a side cross-sectional view, FIG. 19c is a first end view, and FIG. 19d is a second end view.

FIG. 20a is a side perspective view, FIG. 20b is a side cross-sectional view, FIG. 20c is a first end view, and FIG. 20d is a second end view.

FIG. 21a is a side perspective view, and FIG. 21b is a side cross-sectional view.

FIGS. 22a–d are various view of the safety valve hub and gas diffuser sleeve in accordance with the fifth embodiment of the present invention. FIG. 22a is a side perspective view, FIG. 22b is a side cross-sectional view, FIG. 22c is a first end view, and FIG. 22d is a second end view.

FIG. 23a is a side perspective view, FIG. 23b is a side cross-sectional view, FIG. 23c is a first end view, and FIG. 23d is a second end view.

FIG. 24a is a side perspective view, FIG. 24b is a side cross-sectional view, FIG. 24c is a first end view, and FIG. 24d is a second end view.

FIGS. 25a–f are various view of the spring tensioner and lock teeth in accordance with the fifth embodiment of the present invention. FIG. 25a is a side perspective view, FIG. 25b is a side cross-sectional view rotated 90 degrees from FIG. 25a, FIG. 25c is a first end view, FIG. 25d is a second end view, FIG. 25e is a first end view rotated 90 degrees from FIG. 25c, and FIG. 25e is a second end view rotated 90 degrees from FIG. 25d.

FIGS. 26a–d are various view of the actuator button with dual fork structure in accordance with the fifth embodiment of the present invention. FIG. 26a is a side perspective view, FIG. 26b is a side cross-sectional view, FIG. 26c is a first end view, and FIG. 26d is a second end view.

FIG. 27a is a side perspective view, FIG. 27b is a second side perspective view rotated 90 degrees from FIG. 27a, FIG. 27c is a side cross-sectional view, FIG. 27d is a second side cross-sectional view rotated 90 degrees from FIG. 27c, FIG. 27e is a first end view, FIG. 27f is a first end view rotated 90 degrees from FIG. 27e, FIG. 27g is a second end view and FIG. 27h is a second end view rotated 90 degrees from FIG. 27g.

FIGS. 28a–d are various view of the safety clamp in accordance with the fifth embodiment of the present invention. FIG. 28a is a top plan view, FIG. 28b is a side perspective view, FIG. 28c is a first end view, and FIG. 28d is a second end view.

DETAILED DESCRIPTION OF THE PREFERRED EMBODIMENTS

Figure 2:
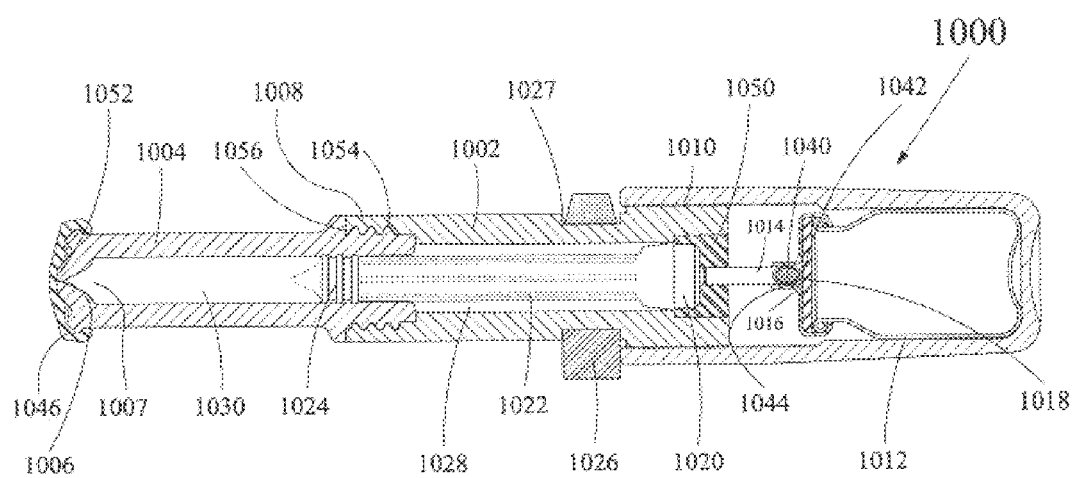
FIG. 2 is a cross-sectional diagram of the needle-less injector device with the gas power source as shown along the line 2—2 in FIG. 1.
Figure 1:
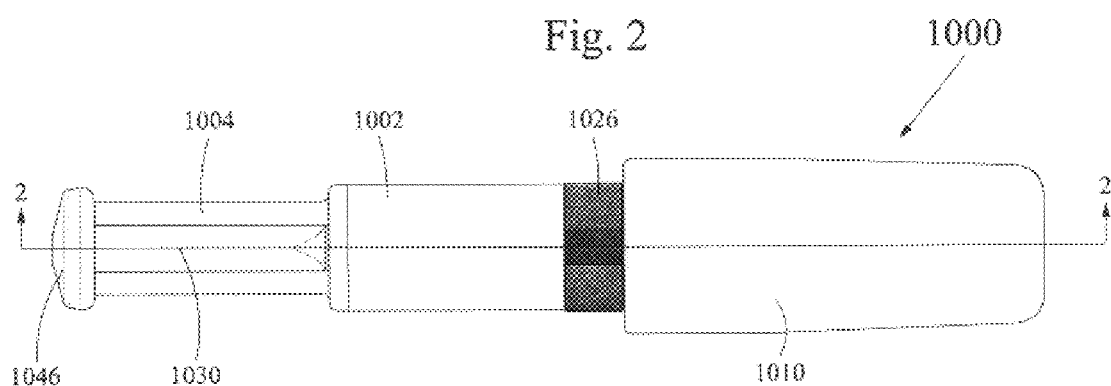
FIG. 1 is a perspective view of an needle-less injector device with an improved gas power source according to a first embodiment of the invention.
Figure 5A:
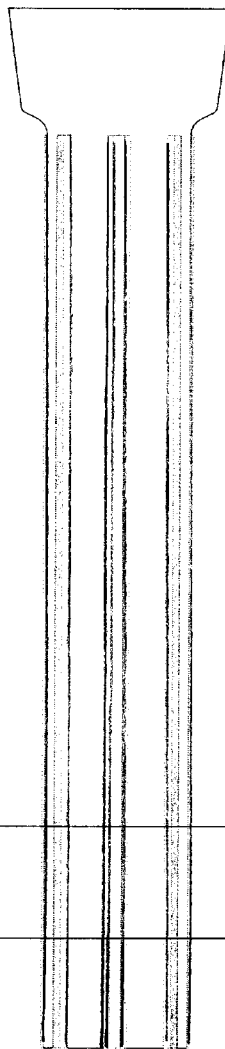
Figure 5B:
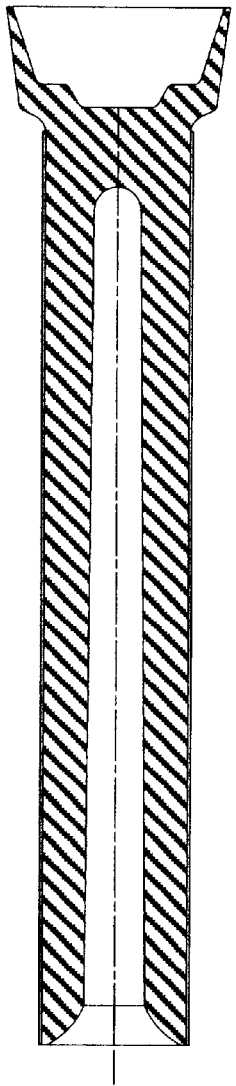
Figure 6D:
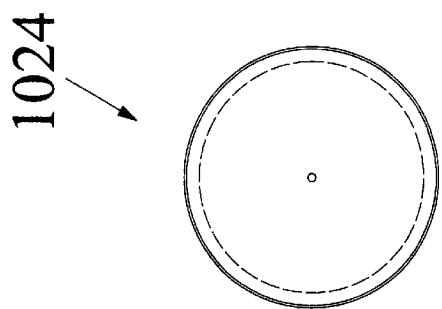
FIGS. 6a–d are various views of the plunger in accordance with the first embodiment of the present invention.
Figure 6B:
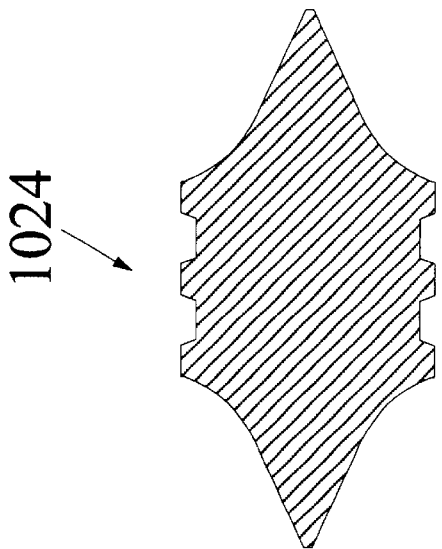
Figure 6A:
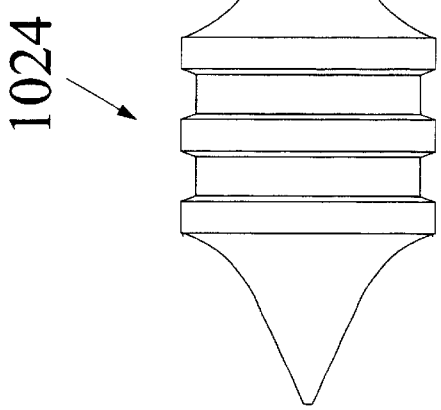
Figure 6C:
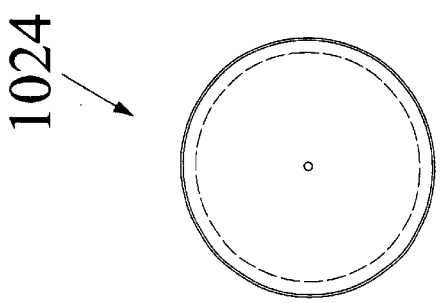
Figure 8A:
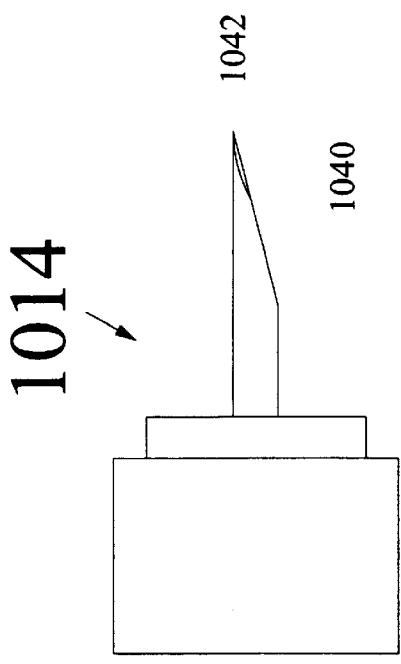
FIGS. 8a–d are various view of the piercing cannula in accordance with the first embodiment of the present invention.
Figure 8D:
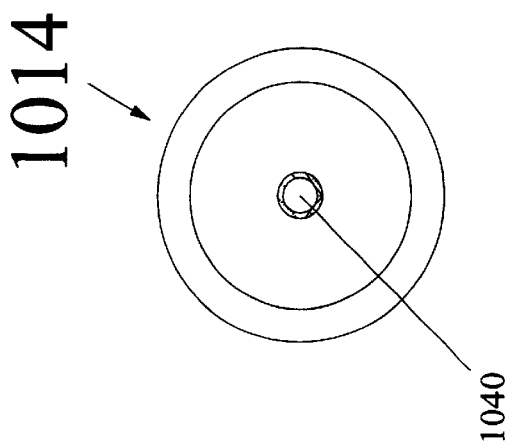
Figure 8B:
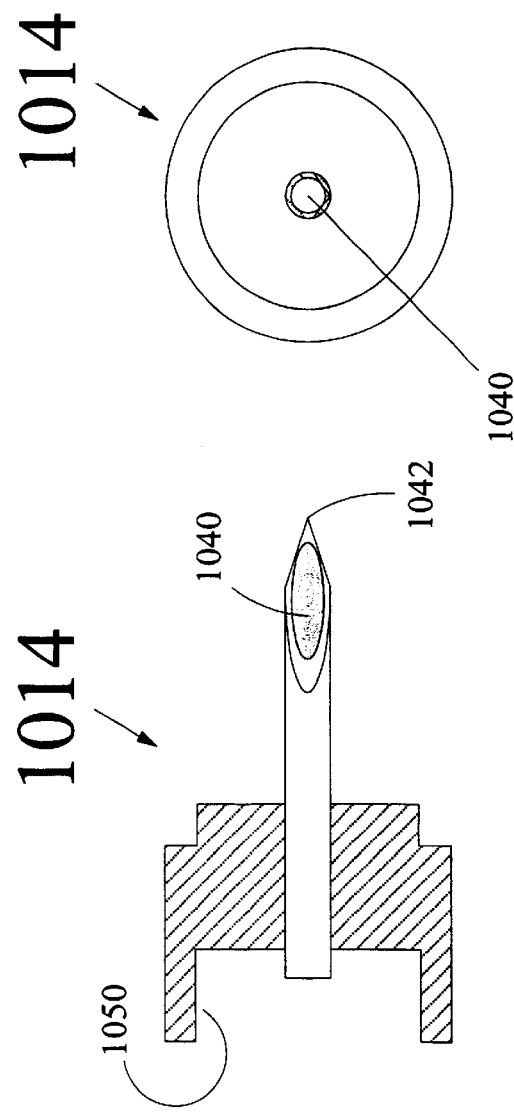
Figure 8C:
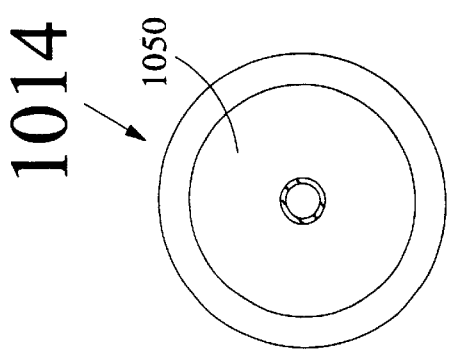
Figure 9D:
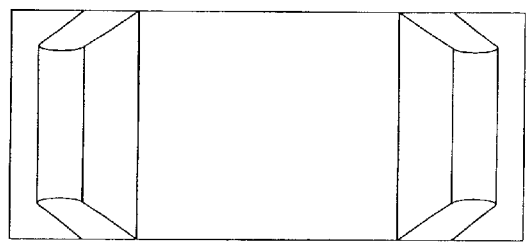
Figure 9A:
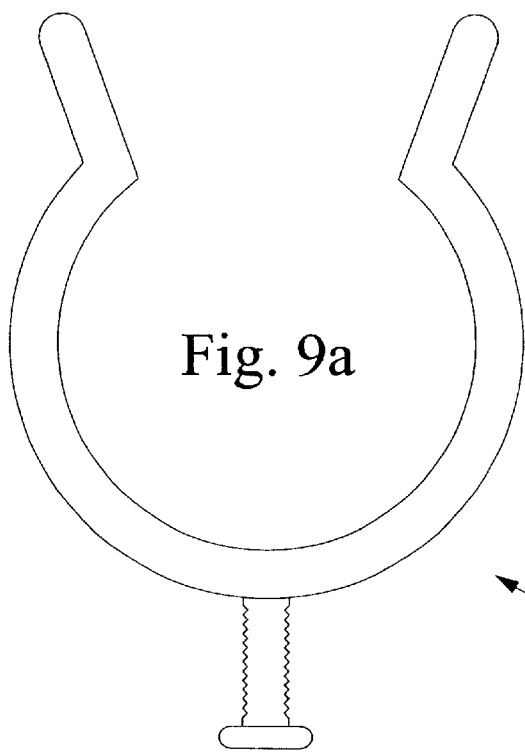
Figure 9C:
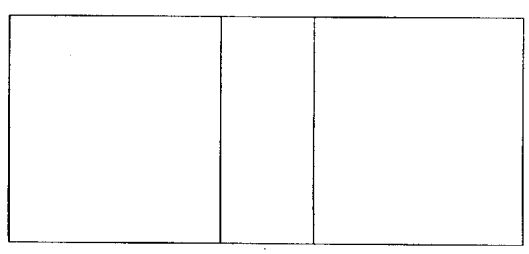

As shown in the drawings for purposes of illustration, the invention is embodied in an improved gas power source for a single-use needle-less injector containing medication. Generally, the improved gas power source is used in conjunction with, or are attached to, a single-use disposable needle-less injector, such as that disclosed in U.S. patent application Ser. No. 09/215,769 filed Dec. 19, 1998, now U.S. Pat. No. 6,063,053 U.S. patent application Ser. No. 08/719,459 filed Sep. 25, 1996, now U.S. Pat. No. 5,730,723, Ser. No. 08/727,911 filed Oct. 9, 1996, now U.S. Pat. No. 5,851,198 and U.S. patent application Ser. No. 09/192,079 filed Nov. 14, 1998, now U.S. Pat. No. 6,080,130, which are herein incorporated by reference, or preferably with the needle-less injectors as described below. However, it will be recognized that further embodiments of the invention may be used in multiple use needle-less injectors that utilize replaceable gas power sources after each use and in other devices that require an accurate gas discharge release or the like. Still further embodiments may use the disclosed needle-less injectors with other activation methods including pyrotechnic power sources, spring power sources, or the like.

In preferred embodiments of the present invention, a gas powered needle-less injector device is pre-loaded with medication and is adapted for a single use. Preferably, the needle-less injector is for use with human beings. However, it will be recognized that further embodiments of the invention may be used on animals or in other applications requiring needle-less injection, such as passing injectable substances through a porous membrane or the like. Also, embodiments of the present invention may be used to inject other fluids or in etchants, such as proteins, vitamins, hormones, drugs, vaccines, medications, lyophilized medications, medication cocktails, or the like. It should be understood that reference in later sections of the application to fluid, medication, injectant, or the like, should not be vied as limiting the embodiment to the recited fluid, medication, injectant, or the like, and should be understood to include any fluid, injectant, medication, or the like mentioned in the application herein.

A needle-less injection device according to an embodiment of the invention is embodied in a pen sized device. The needle-less injector device 1000 according to an embodiment of the invention is useful for hypodermic injection of medication without piercing the skin (non-invasive) with a needle and represents an improvement over known devices by the use of an improved gas power source. The injector device 1000 may be used as a single dose disposable injector to deliver a dosage of fluid medication. The preferred embodiment ensures precise delivery through an orifice with the diameter of approximately 0.0032" (approximately 0.08 mm). However, larger or smaller diameters, ranging from 0.05 mm to 1.5 mm, may be used, as long as accurate penetration of the skin and delivery of the medication can be maintained. The fluid is linearly accelerated via pneumatic propulsion. Safety is maintained and inadvertent activation of the injector device 1000 is avoided via a pressure (e.g., resistance) sensitive triggering feature which allows for proper tensioning of the nozzle and orifice at the injection site prior to automatic medication deployment. For example, activation of the injector device 1000 will not occur until the injector is properly positioned to provide the required resistance from the skin surface of the patient to allow for sufficient tension and pressure to be applied to a trigger of the injector device 1000 to activate it to deliver the dosage of medication. Improper positioning, resulting in insufficient resistance by the skin surface of the patient will prevent the injector device 1000 from being inadvertently activated. For example, tight tolerances between a trigger cap and a housing can prevent the cap from sliding along the housing to trigger the injector device 1000, if the injector device 1000 is more than 10 degrees off of an axis perpendicular to the skin surface of the patient.

The device 1000 utilizes prepackaging and precisely measured dosages for a variety of medical applications. However, alternative embodiments may be loaded just prior to injection. The injector device 1000 can be manufactured in various custom sizes for precise medication delivery over a wide range of medication types and dosage amounts. Preferred embodiments allow for a single injection in amounts that range from about ½0th of one cubic centimeter (cc) to 1.0 cc. The type of injector device 1000 is typically used on human patients. However, in alternative embodiments, a larger injector device with larger medication capacity may be constructed and used on animals, such as livestock or the like.

FIGS. 1–9e illustrate a needle-less injector 1000 in accordance with a first embodiment of the present invention. The needle-less injector 1000 includes a main housing 1002, an ampoule 1004 having an orifice 1006. The ampoule 1004 includes an open end 1008 that mates with the main housing 1002 through adhesives, welding snap fits, or the like. In alternative embodiments, as shown in FIGS. 3a–3g, the ampoule 1004 is formed as an integral part of the main housing 1002. An actuator cap 1010 mates with the main housing 1002, and a sealed gas charge (or power source) 1012 is contained within the actuator cap 1010. A piercing cannula 1014 is secured to the main housing 1002, and cooperates with a cannula guide 1016 coupled to the gas charge 1012 to guide the piercing cannula 1014 to pierce a diaphragm 1018 that seals in the gas charge 1012. A plunger chamber 1020 works with the other end of the piercing cannula 1014 to assure even distribution of gas pressure when the sealed gas is released from the gas charge 1012. A plunger shaft 1022, that when gas is released, slides within a bore 1028 of the main housing 1002 through the open end 1008 and a bore 1030 of the ampoule 1004 to cause fluid to be expelled through the orifice 1006. A plunger 1024 contained in the ampoule 1004, that fits at the end of the plunger shaft 1022, is moveable by the plunger shaft 1022 and seals the fluid within the ampoule 1004. In preferred embodiments, the main housing 1002, and actuator cap 1010, plunger shaft 1022, cannula guide 1016 are made of polycarbonate, or other suitable materials, such as plastic, metal, composites, ceramics or the like. The piercing cannula 1014 is formed from metal. However, other materials, such as plastic, glass, composites, laminates, ceramics, glass, or the like, may be used.

Thus, the needle-less injector 1000 has an orifice end that includes orifice 1006 and a trigger end that includes the actuator cap 1010. The plunger shaft 1022 is slidably disposed within a bore 1028 of the main housing and the interior bore 1030 of the ampoule 1004. As shown in FIGS. 3a–4d, the actuator cap 1010 includes 4 spline slots 1032 that mate with corresponding 4 splines 1034 on the exterior of the main housing 1002. The spline slots 1032 and splines 1034 cooperate to maintain the orientation of the actuator cap 1010 to the main housing 1002. In alternative embodiments, more or less splines may be used, the splines and slots may be interchanged, or other methods of maintaining the orientation of the actuator cap 1010 and the main housing 1002 in position may be used. In preferred embodiments, the splines 1032 and spline slots 1034 have a rectangular cross-section. However, in alternative embodiments, the splines and spline slots may have other cross-sections, such as triangular, saw tooth, dove tail or the like, to resist rotational movement of the actuator cap 1010 about the main housing 1002.

The actuator cap 1010 also includes at least one ratchet track 1036 that mates with a corresponding ratchet receiving track 1038 on the main housing 1002 to permit the actuator cap 1010 to move towards the ampoule 1004 and to prevent movement of the actuator cap 1010 away from the ampoule during use of the device or during transport. Preferably, the teeth of the ratchet track 1036 and ratchet receiving track 1038 are saw tooth, with the ramped side towards the ampoule 1004. However, alternative embodiments, may use different teeth configurations that perform the same function, or may use additional ratchet tracks and ratchet receiving tracks, with the selection being dependent on tolerances between the parts of the injector 1000, the force desired to compress the actuator cap 1010 when pressed against the skin, the force exerted on the actuator cap 1010 when the gas from the gas charge 1012 is expelled, or the like. If at least the ratchet track 1036 and/or the ratchet receiving track 1038 extend around the entire periphery of the actuator cap 1010 and/or main housing 1002, orientation may not need to be maintained and the splines may be omitted. In alternative embodiments, the splines, the spline slots, the ratchet tracks and the ratchet receiving tracks may be combined together so that the splines and spline slots include the ratchet teeth.

As the actuator cap 1010 is moved towards the ampoule 1004, the gas charge 1012 is also moved towards the ampoule 1004 and the piercing cannula 1014. The piercing cannula 1014 includes a gas bore (or channel) 1040 formed in the piercing cannula 1014 to act a conduit to direct the expelled gas into the plunger chamber 1020 to act on the plunger shaft 1022. The piercing cannula 1014 includes a sharp tip 1042 to pierce the diaphragm 1018 of the gas charge 1012. In preferred embodiments, the gas bore 1040 opens up through the sharp tip 1042. However, in alternative embodiments, the sharp tip is solid and includes one or more side ports that provide communication to the gas bore 1040. This design might be desirable if the material forming the diaphragm 1018 of the gas charge 1012 could clog the gas bore 1040. The sharp tip 1042 of the piercing cannula 1014 is contained in a guide bore 1044 formed in the cannula guide 1016 to direct the cannula 1014 to the diaphragm 1018 of the gas charge and to prevent the piercing cannula 1014 from shifting during transport and activation. The other end of the cannula guide 1016 is adapted to attached, by snap fit, threads, detents and slots, adhesives, or the like, to the gas charge 1012.

In preferred embodiments, the diaphragm 1018 is a thin laminate of plastic backed with metal foil that closes off and seals the gas charge 1012. In alternative embodiments, the diaphragm is a frangible metal disk, thin pierceable metal or foil, elastomeric material (such as rubber, plastic or the like), composites, laminates, ceramics, thin glass, or the like. In preferred embodiments, the gas contained in the gas charge 1012 is $CO_2$. However, alternative embodiments, may use other gas, such as air, nitrogen, noble gases, mixtures, liquid/gas combinations, or the like. In a preferred embodiment, the container of the gas charge 1012 is formed from metal. However, other materials, such as plastic, glass, composites, laminates, ceramics, glass, or the like, may be used. In addition, preferred embodiments have a convex bottom as shown in FIGS. 2 and 7c. However, alternative embodiments may use a flat bottom as shown in FIG. 7b or other shapes adapted to mate with the injector device and maintain structural integrity of the gas charge 1012 prior to use.

In preferred embodiments, as shown in FIGS. 5a–g, the plunger shaft 1022 has one end inverted cone shaped to receive and seat the corresponding shape of the plunger 1024, and the other end is convex shaped to receive the gas from the gas charge 1012. In alternative embodiments, the front and rear surfaces may be flat, or have other suitable shapes. The plunger shaft 1022 is disposed inside the bore 1028 of the main housing 1022 and the bore 1030 of the ampoule 1004 for sliding movement along their length. In preferred embodiments, one end of the plunger shaft 1022 has substantially the same outer diameter as the inner diameter of the bore 1028 of the main housing 1002 and the other end of the plunger shaft 1022 has substantially the same outer diameter as the inner diameter of the bore 1030 of the ampoule 1004 to provide free sliding movement of the plunger shaft 1022 along the length of the bore 1028 and bore 1030. This also forms an air and fluid tight seal with a minimal friction between the plunger shaft 1022 and the walls of the bore 1028 and 1030.

Preferably, the plunger 1024 is formed of an elastomeric material, such as rubber or plastic, or the like. Also, the plunger 1024 is preferably shaped to fit within a matched recess in the end of the plunger shaft 1022 to minimize twisting or jamming during activation, and matches the shape of the orifice 1006 to minimize left over fluid at the end of an injection and to maintain the velocity of the escaping fluid throughout the injection. The plunger 1024 has an outer diameter which is substantially the same as the inner diameter of the bore 1030 of the ampoule 1004. The plunger 1024 is disposed between the plunger shaft 1022 and the orifice 1006. The medication (or fluid) is situated in front of the plunger 1024 (i.e., between the orifice 1006 and the plunger 1024) so that forward movement of the plunger 1024 forces the liquid medication toward the orifice 1006. The front surface of the plunger 1024 may be configured to match the opening defined by an orifice guide 1007. In preferred embodiments, the front surface of the plunger 1024 has a convex surface to match the concave shape of the orifice guide 1007, whose vertex is the orifice 1006. The shape of the orifice guide 1007 focuses and increases the speed of medication as it exits the orifice 1006. The matching shapes of the orifice guide 1007 and the plunger 1024 tend to minimize the waste of medication, since most of the medication is forced out through the orifice 1006. The shape of the rear surface of the plunger 1024 matches the front surface of the plunger shaft 1022. The similarly shaped configuration provides for an even distribution of the pressure on the rear of the plunger 1024 when the plunger shaft 1022 moves forward. This tends to minimize jams or distortion as the plunger 1024 is driven forward. Preferably, the plunger shaft 1022 and the plunger 1024 are formed as separate pieces. However, in alternative embodiments, the plunger shaft 1022 and the plunger 1024 are formed as an integrated piece either by attaching the plunger 1024 to the plunger shaft 1022 or by molding the plunger shaft 1022 to include the plunger 1024.

In addition, a protective cap 1046 that covers the orifice 1006 of the ampoule can be a hard material, such as plastic, metal or the like, or a soft generally compliant rubber material. The protective cap 1046 is generally snapped onto the end of the ampoule 1004. However, alternative embodiments may utilize threads. The protective cap 1046 may be mounted on the end of the ampoule 1004 to cover the orifice 1006. The protective cap 1046 provides and maintains sterility of the injector device 1000 and prevents an accidental discharge of the liquid medication disposed within the bore 1030 of the ampoule 1004 from shock, evaporation or seepage.

A safety clip 1026 is also included to prevent premature activation of the needle-less injector 1000 by fitting in a recess 1027 formed in the main housing 1002 to prevent the actuator cap 1010 from sliding forward and activating the gas charge 1012. Further, the safety clip 1026 can be a hard material, such as plastic, metal or the like, or a soft generally compliant rubber material, if it can resist movement of the actuator cap 1010 towards the ampoule 1004.

To use the needle less injector 1000, the user removes the protective cap 1046 that covers the orifice 1006 of the ampoule 1004. The user also removes the safety clip 1026. Next, the user places the orifice 1006 and end of the ampoule 1004 against the tissue (such as skin, organs, different skin layers or the like) so that the needle-less injector 1000 is generally perpendicular to the tissue, as described above. The user then presses on the actuator cap 1010 to move it towards the ampoule 1004. The actuator cap 1010 moves after a predetermined force threshold is reached and the tissue resists further forward movement of the injector 1000. As the actuator cap 1010 moves along the main housing 1002, the ratchet track 1036 and ratchet receiving track 1038 engage to permit forward movement of the actuator cap 1010, but to inhibit rearward movement. Also, as the actuator cap 1010 moves towards the ampoule 1004, the gas charge 1012 and cannula guide 1016 are moved towards the sharp tip 1042 of the piercing cannula 1014, which eventually pierces the diaphragm 1018 to release the gas in the gas charge 1012. As the gas is released from the gas charge 1012, the ratchet track 1036 and ratchet receiving track 1038 resist rearward movement of the actuator cap 1010. The gas then flows down the gas bore 1040 in the piercing cannula 1014 filling the plunger chamber 1020, and then presses on the plunger shaft 1022. As the released gas escapes, the pressure quickly increases to drive the plunger shaft 1022 forward, which in turn drives the plunger 1024 forward towards the orifice 1006 in the ampoule 1004. As the plunger 1024 travels forward, fluid is expelled out of the orifice 1006 to pierce the tissue and deliver the fluid below the surface of the tissue.

Generally, upon activation of the needle-less injector device 1000, the gas is released from the gas charge 1012 to reach an initial pressure peak of approximately 1800 psi in approximately 8–9 milliseconds. During the delivery phase the pressure drops to approximately 1200 to 1600 psi. Preferably, during the delivery phase, the pressure is not constant. After completion of the injection, the pressure gradually decreases as the gas escapes back through the seals around the cannula device and the actuator cap 1010. In alternative embodiments, different pressure profiles may be used with higher pressures, such as up to 2500 psi, and lower pressures, such as down to 400 psi, with the selection being determined by orifice size, fluid viscosity, desired injection speed, desired injection depth, or the like. Also, preferred embodiments use a hollow plunger shaft 1022 (as shown in FIGS. 5a–g) to provide a cavity for the gas to enter into after the plunger 1024 has completed the injection. Further embodiments may include a pressure vent that is exposed by the plunger shaft 1022 after it has moved forward and completed the injection.

In preferred embodiments, the main housing 1002 and the ampoule 1004 each has an elongated cylindrical shape. However, in alternative embodiments, other shapes such as rectangular, triangular or the like may be used. The main housing 1002 also has the bore 1028 centrally disposed along the length of the main housing 1002 and the ampoule 1004 has the bore 1030 centrally disposed along the length of the ampoule 1004. The bore 1028 and bore 1030 each has a cylindrical shape. However, in alternative embodiments, other shapes such as rectangular, triangular or the like may be used. The base 1050 of the piercing cannula 1014 gradually tapers off as the plunger chamber 1020 nears the piercing cannula 1014. The smaller diameter portions of the base 1050 limits the backward movement of the plunger shaft 1022 and tends to increase the rate of acceleration when the injector device 1000 is first activated. In alternative embodiments, the smaller diameter portions of the base 1050 are omitted and a hard stop (not shown) is used to limit rearward movement of the plunger shaft 1022. This would have the advantage of minimizing the volume available for escaping gases from the gas charge 1012 to expand onto the plunger shaft 1022 prior to moving the plunger shaft 1022 forward.

The ampoule 1004 includes the bore 1030 for storing and holding, for example, liquid medication (not shown). The bore 1030 has the orifice 1006 (or nozzle) at one end and has the open end 1008 to receive the plunger 1024 at the other end. The orifice 1006 is centrally positioned on an injector face 1052. The injector face 1052 has a flat surface, except that the center region around the orifice 1006 is raised slightly. The raised surface around the orifice 1006 provides firm contact against a receiving surface, such as the skin surface (not shown). This helps to insure that the injector device 1000 is properly positioned and will not be activated until sufficient pressure is applied to the injector device 1000.

In preferred embodiments, the open end 1008 of the ampoule 1004 has threads 1054 on the outer diameter and matching threads 1056 are formed inside of the main housing 1002 to screw-in the ampoule 1004. Although not shown in the drawings, an O-ring may be placed between the ampoule 1004 and the main housing 1002 to provide an additional air and fluid tight seal. Using separate parts provides the advantage of being able to assemble the injector device 1000 when needed or just prior to giving an injection. Also, the injector device 1000 can be disassembled as desired. This assembly option allows the user to select a variety of different medications or dosages while minimizing the number of complete injector devices 1000 that must be carried or stocked. In addition, a user could store the ampoule 1004 in different environments, such as a refrigerator for perishable medications and minimizes the refrigerated storage space, since the rest of the injector device 1000 does not require refrigeration. It would also facilitate manufacture of the injector device 1000, since the injector device 1000 and the ampoule 1004 may be manufactured at different times. Alternatively, as shown in FIGS. 3a–3g, the ampoule 1004 is formed as an integral part of the main housing 1002. This would reduce the number of molded parts and the overall cost of the injector device 1000, but would reduce flexibility.

For easy measuring and observation of the amount of medication in the ampoule 1004, the outer surface of the ampoule 1004 can include graduations (not shown) so that the user can determine the amount of medication contained in the injector device 1000. The ampoule 1004 can be formed of glass or other suitable materials, such as plastic, ceramic, polycarbonate or the like. In a preferred embodiment, the ampoule 1004 is transparent so that the liquid medication and the various moving parts in the ampoule 1004 can be visually examined. Also, the ampoule 1004 is disposable. However, in alternative embodiments, the ampoule 1004 may be recycled, if desired.

A resistance sensitive trigger includes the actuator cap 1010 that is an elongated tubular member that slides over the main housing 1002. The actuator cap 1010 is closed at one end and has an opening at the other end. On the inner surface are the ratchet teeth of the ratchet tracks 1036 that engage with the corresponding ratchet receiving tracks 1038. The proper use of the injector device 1000 requires that the injector device 1000 be positioned substantially perpendicular to the skin surface before the medication is injected into the injection site. Therefore, the resistance to movement of the ratchet teeth of the ratchet tracks 1036 and the ratchet receiving tracks 1038 towards the orifice 1006 should be sufficiently strong to prevent accidental triggering when the injector device 1000 is not properly positioned. Typically, a minimum applied pressure of 2.2 lbs/in$^2$ (1.0 kg/2.5 cm$^2$) is required to discharge the injector. However, slightly lower or higher minimums may be required depending on the skin of the patient or where the injection is to be administered. In alternative embodiments, alternate resistance elements or resilient members may be used instead of the ratchet tracks 1036 and ratchet receiving tracks 1038, such as deformable rubber or plastic, or the like.

Figure 10:
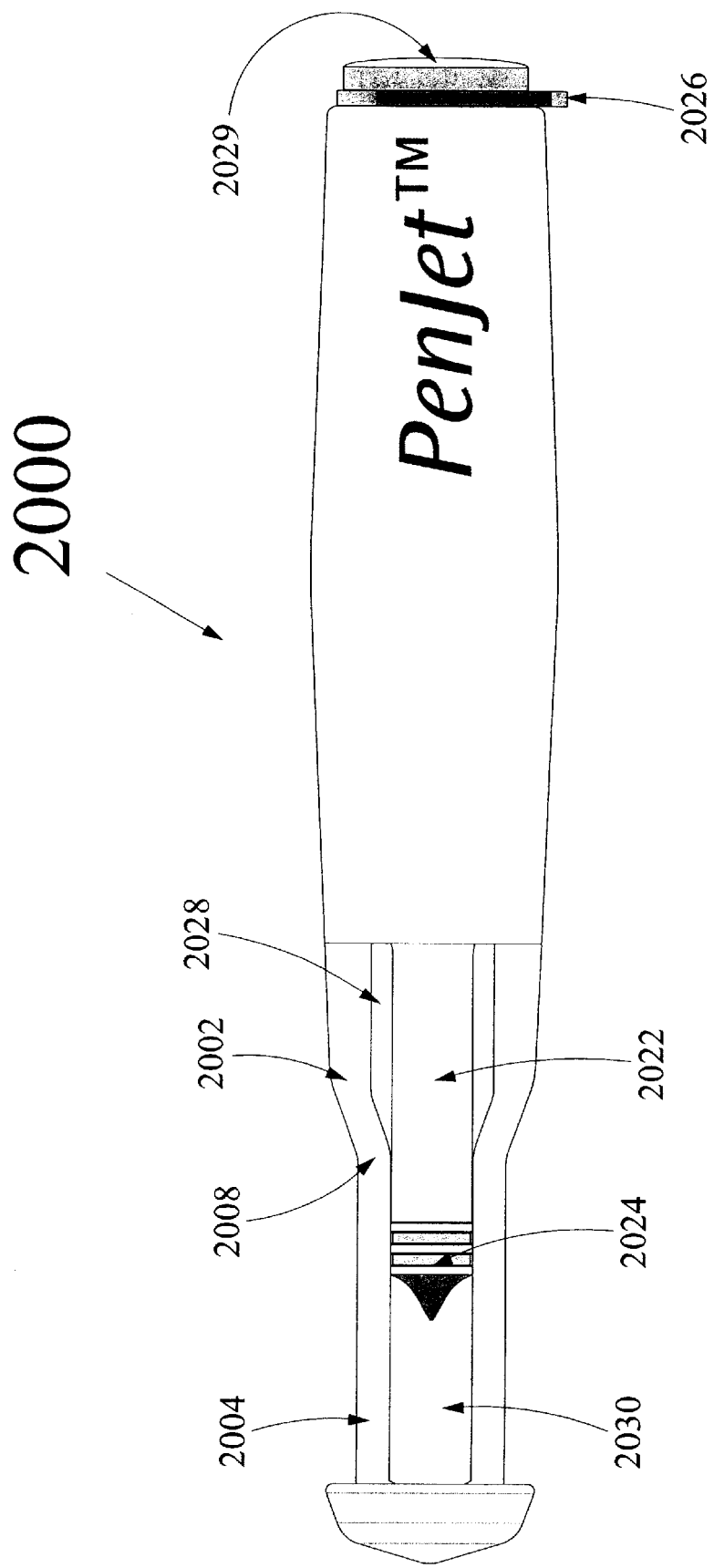
FIG. 10 is a side perspective view of needle-less injector that utilizes a gas power source in accordance with a second embodiment of the present invention.
Figure 11:
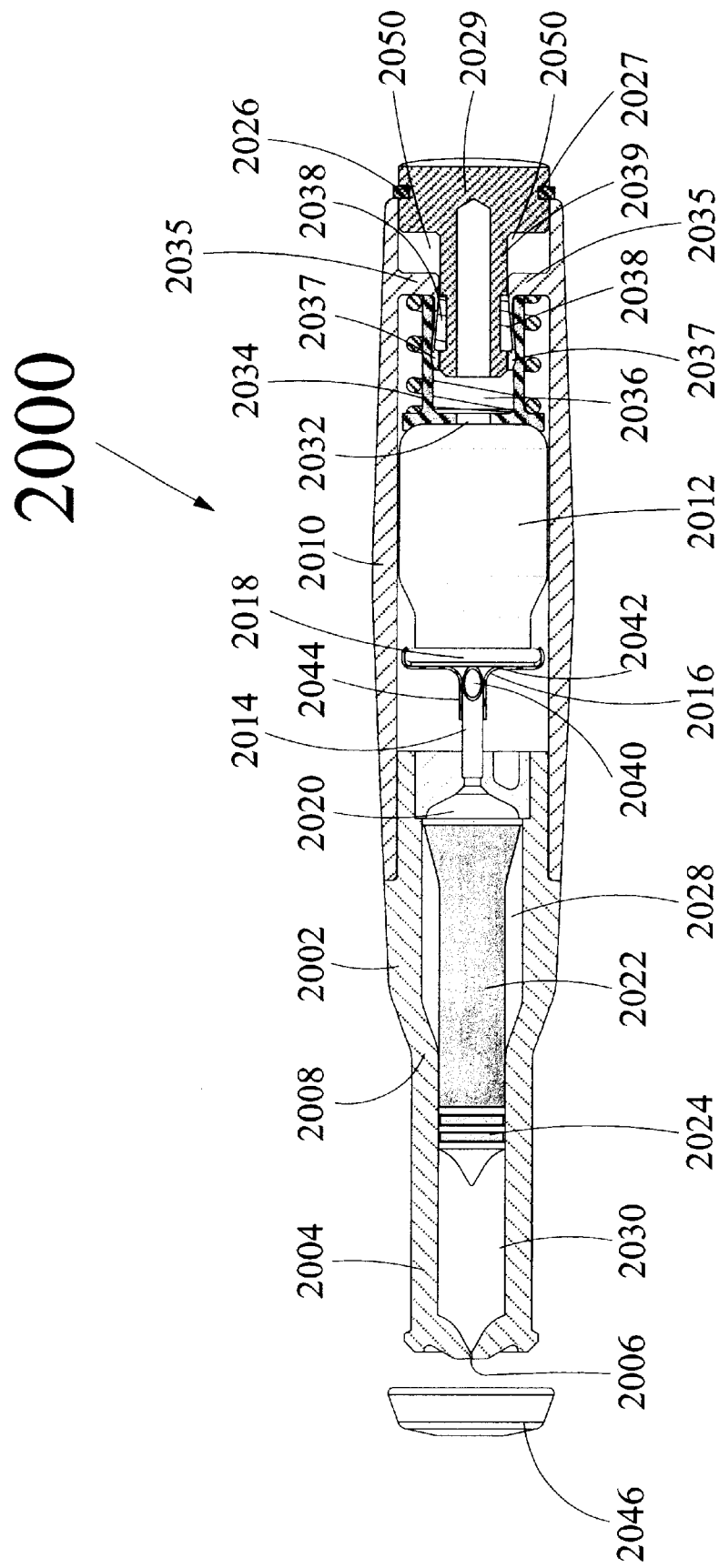
FIG. 11 is a cross-sectional diagram of the needle-less injector and power source as shown along the line 11—11 in FIG. 10.

FIGS. 10 and 11 illustrate a needle-less injector 2000 in accordance with a second embodiment of the present invention. Various features and aspects of the first embodiment may be combined with and/or used with this embodiment. The needle-less injector 2000 includes a main housing 2002, an ampoule 2004 having an orifice 2006. The ampoule 2004 includes an open end 2008 formed integrally with the main housing 2002. An actuator cap 2010 mates with the main housing 2002, and a sealed gas charge (or power source) 2012 is contained within the actuator cap 2010. A piercing cannula 2014 is secured to the main housing 2002, and cooperates with a cannula guide 2016 coupled to the gas charge 2012 to guide the piercing cannula 2014 to pierce a diaphragm 2018 that seals in the gas charge 2012. A plunger chamber 2020 works with the other end of the piercing cannula 2014 to assure even distribution of gas pressure when the sealed gas is released from the gas charge 2012. A plunger shaft 2022, that when gas is released, slides within the main housing 2002 through the open end 2008 of the ampoule 2004 to cause fluid to be expelled through the orifice 2006. A plunger 2024 contained in the ampoule 2004, that fits at the end of the plunger shaft 2022, is moveable by the plunger shaft 2022 and seals the fluid within the ampoule 2004. A safety clip 2026 is also included to prevent premature activation of the needle-less injector 2000 by fitting in a recess 2027 formed in the actuator cap 2010 to prevent an actuator button 2029 from sliding forward and activating the gas charge 2012.

Thus, the needle-less injector 2000 has an orifice end that includes orifice 2006 and a trigger end that includes the actuator button 2029 in the actuator cap 2010. The plunger shaft 2022 is slidably disposed within a bore 2028 of the main housing and the interior bore 2030 of the ampoule 2004. The actuator cap 2010 is fixed to the main housing 2002 to maintain the orientation of the actuator cap 2010 to the main housing 2002. The gas charge 2012 is disposed inside of the actuator cap 2010 and has a tab lock 2032 that engages with a spring retainer 2034 that is used to move the gas charge towards the piercing cannula 2014. In other alternatives, the gas charge 2012 may omit the tab lock 2032 and be attached to the spring retainer 2034 by other methods such as adhesives, snap fits, nuts and bolts, rivets, two-sided tape, or the like. The spring retainer 2034 is moved by a spring 2036. Alternatively, the spring retainer 2034 may be moved forward by other expansive materials, such as rubber, foam, plastic, or the like. The spring retainer 2034 is held in position, prior to activation, by lock teeth 2037 (flexible in a manner similar to leaf springs) that are formed on the inside of the actuator cap 2010. The lock teeth 2037 are held in position by an actuator shaft 2039 of the actuator button 2029. The actuator shaft 2039 is formed with a circumferential recess 2038 sized to receive the lock teeth 2037 when the actuator button 2029 is depressed and the actuator shaft 2039 and recess 2038 slide past the ends of the lock teeth 2037. The lock teeth 2037 also serve to retain the actuator button 2029 in the depressed position after the injection by inhibiting rearward movement of the actuator shaft 2039 and recess 2038.

To assemble the gas power source assembly, the gas charge 2012 is attached to the spring retainer 2034 by the lock tab 2032. The spring 2036 is placed around and against the end of the spring retainer 2034. The gas charge 2012, spring retainer 2034 and spring 2036 are inserted into the actuator cap 2010 and pressed back against stops 2035 to place the spring 1036 under tension. This assembly is then held in place during the rest of the assembly process. Next, the safety clip 2026 is attached to the recess 2027 on the actuator button 2029 to prevent the actuator button 2029 from being inserted too far in the actuator cap 2010 during the insertion process. The actuator button 2029 and actuator shaft 2039 are slid into the actuator cap 2010 so that the actuator shaft 2039 presses the lock teeth 2037 into the spring retainer 2034 to secure it in position prior to activation. Preferably, the actuator shaft 2039 and actuator button 2029 are retained in the actuator cap 2010 by friction. In alternative embodiments, the end of the actuator shaft 2039 may include small barbs (not shown) that slide past the ends of the lock teeth 2037 to prevent the actuator shaft 2039 and actuator button 2029 from being removed from the actuator cap 2010 after assembly. In further alternative embodiments, the interior of the actuator cap 2010 may include small bumps or detentes that help secure the gas charge 2012 in position after assembly, but which do not hinder the movement of the gas charge 2012 by the spring 2036 when the spring retainer 2034 is released. Next, the gas charge 2012 is released and is then held in place by the locked spring retainer 2034. After which the assembly can then proceed with the other injector device components, such as the main housing 2002, ampoule 2004, piercing cannula 2014, plunger shaft 2022, and plunger 2024.

As the actuator button 2029 is moved towards the ampoule 2004, the lock teeth 2037 seat in the recess 2038 of the actuator shaft 2039. This releases the spring retainer 2034 so that the spring 2039 moves the gas charge 2012 towards the ampoule 2004 and the piercing cannula 2014. The piercing cannula 2014 includes a gas bore (or channel) 2040 formed in the piercing cannula 2014 to act as a conduit to direct the expelled gas into the plunger chamber 2020 and to act on the plunger shaft 2022. The piercing cannula 2014 includes a sharp tip 2042 to pierce the diaphragm 2018 of the gas charge 2012. In preferred embodiments, the gas bore 2040 opens up through the sharp tip 2042. However, in alternative embodiments, the sharp tip is solid and includes one or more side ports that provide communication to the gas bore 2040. This design might be desirable if the material of the diaphragm 2018 of the gas charge 2012 could clog the gas bore 2040. The sharp tip 2042 of the piercing cannula 2014 is contained in a guide bore 2044 formed in the cannula guide 2016 to direct the piercing cannula 2014 to the diaphragm 2018 of the gas charge 2012 and to prevent the piercing cannula 2014 from shifting during transport and activation. The other end of the cannula guide 2016 is adapted to be attached, by snap fit, threads, detents and slots, adhesives, or the like, to the gas charge 2012.

In preferred embodiments, the diaphragm 2018 is a laminate of plastic backed with metal foil that closes off and seals the gas charge 2012. In alternative embodiments, the diaphragm is a frangible metal disk, thin pierceable metal or foil, elastomeric material (such as rubber, plastic or the like), composites, laminates, ceramics, thin glass, or the like. In preferred embodiments, the gas contained in the gas charge 2012 is CO2. However, alternative embodiments, may use other gas, such as air, nitrogen, noble gases, mixtures, liquid/gas combinations, or the like. In preferred embodiment, the main housing 2002, actuator cap 2010, plunger shaft 2022, cannula guide 2016, and actuator button 2029 are made of polycarbonate, or other suitable materials, such as plastic, metal, composites, ceramics or the like. The piercing cannula 2014 and container of the gas charge 2012 are formed from metal. However, other materials, such as plastic, glass, composites, laminates, ceramics, glass, or the like, may be used. Preferably, the plunger 2024 is formed of an elastomeric material, such as rubber or plastic, or the like. Also, the plunger 2024 is preferably shaped to fit within a matched recess in the end of the plunger shaft 2022 to minimize twisting or jamming during activation, and matches the shape of the orifice 2006 to minimize left over fluid at the end of an injection and to maintain the velocity of the escaping fluid throughout the injection.

In addition, a protective cap 2046 that covers the orifice 2006 of the ampoule can be a hard material, such as plastic, metal or the like, or a soft generally compliant rubber material. The protective cap 2046 is generally snapped onto the end of the ampoule 2004. However, alternative embodiments may utilize threads. Further, the safety clip 2026 can be a hard material, such as plastic, metal or the like, or a soft generally compliant rubber material, if it can resist movement of the actuator button 2029 towards the ampoule 2004.

To use the needle less injector device 2000, the user removes the protective cap 2046 that covers the orifice 2006 of the ampoule 2004. The user also removes the safety clip 2026. Next, the user places the orifice 2006 and end of the ampoule 2004 against the tissue (such as skin, organs, different skin layers or the like) so that the needle-less injector is generally perpendicular to the tissue, as described above. The user grasps the sides of the actuator cap 2010 and then presses on the actuator button 2029 to move it towards the ampoule 2004. As the actuator button 2029 moves along the actuator cap 2010, the lock teeth 2037 of the actuator cap 2010 seat in the recess 2038 of the actuator button 2029 to release the spring retainer 2034. The spring 2036 then moves the gas charge 2012, cannula guide 2016 and spring retainer 2034 towards the sharp tip 2042 of the piercing cannula 2014, which eventually pierces the diaphragm 2018 to release the gas in the gas charge 2012. As the gas is released from the gas charge 2012, the spring retainer 2034 and spring 2036 resist rearward movement of the gas charge 2012. Preferably, the gas charge 2012 includes sufficient gas to provide sufficient pressure regardless of the position of the gas charge 2012 after it has been pierced by the piercing cannula 2014. The gas then flows down the gas bore 2040 in the piercing cannula 2014 and presses against the plunger shaft 2022. As the released gas escapes, the pressure quickly increases to drive the plunger shaft 2022 forward, which in turn drives the plunger 2024 forward towards the orifice 2006 in the ampoule 2004. As the plunger 2024 travels forward, fluid is expelled out of the orifice 2006 to pierce the tissue and deliver the fluid below the surface of the tissue.

In alternative embodiments, the actuator cap 2010 may include a spring (not shown) in area 2050 between the actuator cap 2010 and the actuator button 2029 to resist depression of the actuator button 2029. In preferred embodiments, a metal spring, made of music wire or the like, with a loaded force of 2.2 lbs/in2 may be used. However, in alternative embodiments, other elastic or expansive materials, such as foam rubber, leaf springs, gas pillows or the like may be used in place of the spring or different spring tensions may be used. This would permit the actuator button 2029 to require a certain pressure to be exerted prior to activation, as opposed to the simple friction present between the actuator shaft 2039 and lock teeth 2037 of the actuator cap 2010. In further embodiments, the top of the actuator button 2029 may be formed as a cap structure (not shown) that slides over and covers the sides of the actuator cap 2010. The safety clip 2026 would then be attached to the actuator cap 2010 in a position to prevent premature depression of the actuator button/cap structure. An advantage of this actuator button/cap structure is that the user grasps the side of the actuator button/cap structure and resistance of the skin (or tissue) as discussed above is used as part of the triggering process.

FIGS. 12a and 12b illustrate an alternative ampoule 3004 in accordance with a third embodiment of the present invention. Various features and aspects of the first and/or second embodiments may be combined with and/or used with this embodiment. FIG. 12a illustrates the ampoule 3004 prior to an injection, and FIG. 12b illustrates the ampoule 3004 after completion of an injection. The ampoule 3004 is useful for holding medications, or the like, that can not be held or stored for long periods of time in plastic or polymer ampoules. The ampoule 3004 includes an orifice 3006, a tubular glass insert 3060, a septum seal 3062 and a plunger septum 3064. Preferably, the housing of the ampoule 3004 is formed from polycarbonate, although other materials may be used. The glass insert 3060 is disposed within the interior of the ampoule 3004. Preferably, the glass insert 3060 is insert molded into the housing of the ampoule 3004, although the glass insert 3060 may be inserted into the ampoule 3004 after it has been molded. The septum seal 3062 is disposed at one end of the glass insert 3060 and the plunger septum 3064 is disposed at the other end of the glass insert 3060 to hold the medication (or fluid) in the glass insert 3060 and define a fluid chamber. Preferably, the septum seal 3062 and the plunger septum 3064 are formed from elastomeric materials that are compatible with the medication that is to be contained in the glass insert 3060. However, alternative embodiments may be formed out of plastics, polymers, laminates, supported metal foils, or the like. To avoid excessive stress on the glass insert 3060 due to temperature, shock, forces encountered when connecting the ampoule 3004 to the rest of the injector device, or the forces generated during the injection, compression dampeners 3068 are installed at the end of the glass insert 3060 and the housing of the ampoule 3004.

The orifice 3006 in the ampoule 3004 also includes a piercing cannula 3066 that is insert molded, or otherwise affixed, into the housing of the ampoule 3004. The piercing cannula 3066 provides a passageway for the medication (or fluid) to flow through the orifice 3006 during the injection. The septum seal 3062 includes a recess 3070 that covers and seals off the medication, or fluid, from the piercing cannula 3066 and orifice 3006 prior to the injection. During an injection, the septum seal 3062 is force forward and is pierced by the piercing cannula 3066 to provide an opening for the medication, or fluid, to escape. The plunger septum 3064 also includes a recess 3072 that prevents the piercing cannula 3066 from penetrating the plunger septum 3064 at the end of the injection. Preferably, the thickness of the septum seal 3062 and plunger septum 3064 are chosen to minimize the amount of medication remaining in the ampoule 3004 at the end of the injection. Preferably, the recesses 3070 and 3072 have circular cross-sections. However, other cross-sections may be used, such as square, triangular, or the like, that may or may not match the shape of the piercing cannula 3066. Preferred embodiments have an opening 3074 at the tip of the piercing cannula 3066. However, alternative embodiments may utilize a solid tip with side ports, as described above.

Figure 13A:
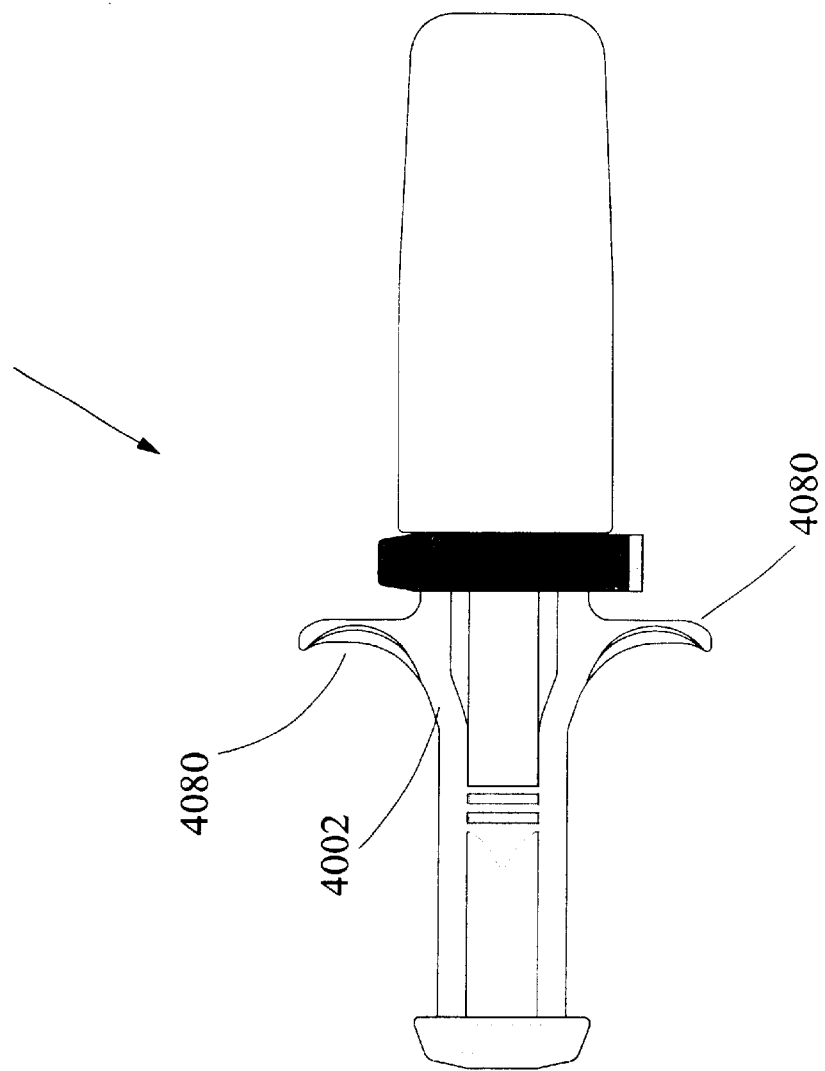
FIGS. 13a and b are various views of a needle-less injector that includes finger rests in accordance with a fourth embodiment of the present invention.
Figure 13B:
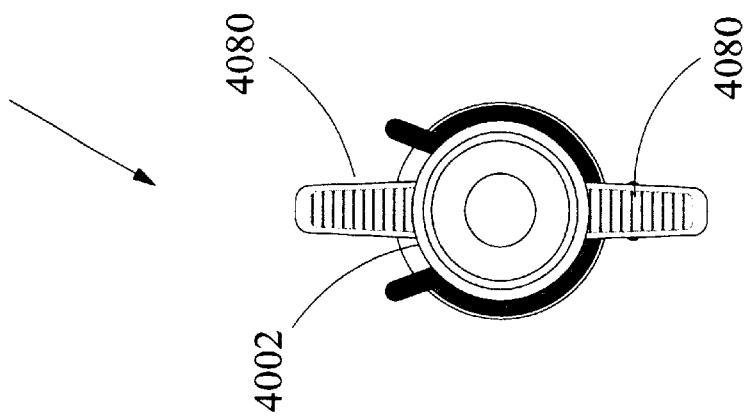
Figure 14:
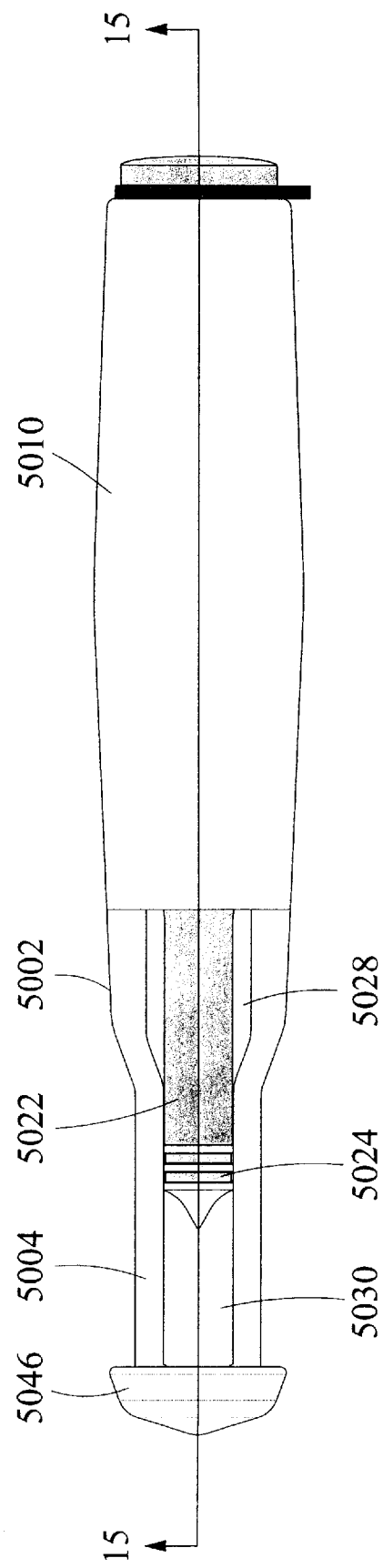
FIG. 14 is a perspective view of an needle-less injector device with an improved gas power source according to a fifth embodiment of the present invention.

FIGS. 13a and 13b illustrate a needle-less injector device 4000 in accordance with a fourth embodiment of the present invention. Various features and aspects of the first, second and/or third embodiments may be combined with and/or used with this embodiment. In this embodiment, the main housing 4002 of the injector device 4000 includes finger rests 4080 that are similar to the finger rests used on ordinary syringes. The finger rests 4080 provide the user with more stability and control over the injector device 4000. The user is no longer required to rely on the resistance of the underlying tissue to activate the device, since the user can depress the actuator cap and/or button and provide support and resistance with the finger rests. However, alternative embodiments, may also utilize the underlying tissue resistance along with the finger rests for greater control.

FIGS. 14a–28d illustrate a needle-less injector 5000 in accordance with a fifth embodiment of the present invention. Various features and aspects of the first through fourth embodiments may be combined with and/or used with this embodiment. The needle-less injector 5000 includes a main housing 5002, an ampoule 5004 having an orifice 5006. The ampoule 5004 includes an open end 5008 formed integral with the main housing 5002. An actuator cap 5010 mates with the main housing 5002, and a sealed gas charge (or power source) 5012 is contained within the actuator cap 5010. A slide valve hub 5014 is secured to the main housing 5002, and cooperates with a barrel valve body 5016 coupled to the gas charge 5012 to guide the slide valve hub 5014 to displace a slideable barrel valve 5018 that seals in the gas charge 5012.

In preferred embodiments, the end 5015 of the slide valve hub 5014 is tapered to match with a corresponding taper in a recess 5017 of the barrel valve body 5016. The taper serves to ease tolerances when the slide valve hub 5014 mates with the barrel valve body and to provide a gas seal between the slide valve hub 5014 and the barrel valve body 5016 during an injection. Preferred tapers are 5°; however, smaller tapers down to 1° and larger tapers up to 45° may be used. A gas diffuser sleeve 5020 works with the slide valve hub 5014 to assure even distribution of gas pressure when the sealed gas is released from the gas charge 5012. Preferably, the gas diffuser sleeve 5020 is formed integrally with the slide valve hub 5014. However, alternative embodiments may be formed from separate pieces.

A plunger shaft 5022, that when gas is released, slides within the main housing 5002 through the open end 5008 of the ampoule 5004 to cause fluid to be expelled through the orifice 5006. A plunger 5024 contained in the ampoule 5004, that fits at the end of the plunger shaft 5022, is moveable by the plunger shaft 5022 and seals the fluid within the ampoule 5004. A safety clip 5026 is also included to prevent premature activation of the needle-less injector 5000 by fitting in a recess 5027 formed in the actuator cap 5010 to prevent an actuator button 5029 from sliding forward and activating the gas charge 5012.

Thus, the needle-less injector 5000 has an orifice end that includes orifice 5006 and a trigger end that includes the actuator button 5029 in the actuator cap 5010. The plunger shaft 5022 is slidably disposed within a bore 5028 of the main housing and the interior bore 5030 of the ampoule 5004. The actuator cap 5010 is fixed to the main housing 5002 to maintain the orientation of the actuator cap 5010 to the main housing 5002. The gas charge 5012 is disposed inside of the actuator cap 5010 and has an adhesive layer 5032 that engages with a spring retainer 5034 that is used to move the gas charge towards the slide valve hub 5014. In other alternatives, the gas charge 5012 may omit the adhesive layer 5032 and be attached to the spring retainer 5034 by other methods such as a lock tab, snap fits, nuts and bolts, rivets, two-sided tape, or the like. The spring retainer 5034 is moved by a spring 5036. Alternatively, the spring retainer 5034 may be moved forward by other expansive materials, such as rubber, foam, plastic, or the like. The spring retainer 5034 is held in position, prior to activation, by lock teeth (or sears) 5037 (flexible in a manner similar to leaf springs) that are formed on a spring tensioner 5035 and engage with a lock recess 5033 of the spring retainer 5034. The lock teeth 5037 are held in position by an actuator shaft 5039 of the actuator button 5029. The actuator shaft 5039 is formed with a dual fork structure 5038 having tines 5038a–d sized and shaped to withdraw the lock teeth 5037 from the spring retainer 5034 when the actuator button 2029 is depressed and the actuator shaft 5039 and dual fork structure 5038 slide over the sear base structure 5031 having tines 5031a–d of the lock teeth 5037. The lock teeth 5037 and the spring tensioner 5035 also serve to retain the actuator button 5029 in the depressed position after the injection by inhibiting rearward movement of the actuator shaft 5039 and recess 5038.

To assemble the gas power source assembly, the gas charge 5012 is attached to the spring retainer 5034 by the adhesive layer 5032. The spring 5036 is placed around and against the end of the spring retainer 5034. The spring tensioner 5035 is slid into the back of the spring retainer 5034 until the lock teeth 5037 engage with a lock recess 5033 in the spring retainer 5035. The gas charge 5012, spring retainer 5034, spring tensioner 5035 and spring 5036 are inserted into the actuator cap 5010 and pressed back against stops 5041 to place the spring 5036 under tension. This assembly is then held in place during the rest of the assembly process.

Next, the safety clip 5026 is attached to the recess 5027 on the actuator button 5029 to prevent the actuator button from being inserted too far in the actuator cap 5010 during the insertion process. The actuator button 5029 and actuator shaft 5039 are slid into the actuator cap 5010 so that the tines 5038a–d of the dual fork structure 5038 of the actuator shaft 5039 passes over the tines 5031*a–d* of the sear base structure 5031 of the lock teeth 5037 to lock the sear base structure 5031 in a set slot 5043 formed in the dual fork structure 5038 to secure it in position prior to activation. Preferably, the actuator shaft 5039 and actuator button 5029 are retained in the actuator cap 5010 by friction. In alternative embodiments, the tines 5038*a–d* of the dual fork structure 5038 and/or of the actuator shaft 5039 may include small barbs (not shown) that slide past the ends of the sear base structure 5031 of the lock teeth 5037 to prevent the actuator shaft 5039 and actuator button 5029 from being removed from the actuator cap 5010 after assembly. In further alternative embodiments, the interior of the actuator cap 5010 may include small bumps or detentes that help secure the gas charge 5012 in position after assembly, but which do not hinder the movement of the gas charge 5012 by the spring 5036 when the spring retainer 5034 is released. Next, the gas charge 5012 is released and is then held in place by the locked spring retainer 5034. After which the assembly can then proceed with the other injector device components, such as the main housing 5002, ampoule 5004, slide valve hub 5014, plunger shaft 5022, and plunger 5024.

As the actuator button 5029 is moved towards the ampoule 5004, the lock teeth 5037 are withdrawn from the lock recess 5033 in the spring retainer 5034 as the tines 5031*a–d* of the sear base structure 5031 of the lock teeth 5037 are moved towards the center-line of the actuator cap 5029 by the inward sloped region 5045 of the recess 5038 of the actuator shaft 5039. The actuator button 5029 is then held in place by the tines 5031*a–d* of the sear base structure 5031 seating and locking in a seat slot 5047 formed at the end of the dual fork structure 5038. After seating in the seat slot 5047, the lock teeth 5037 and the sear base structure 5031 inhibit rearward movement of the spring retainer 5034 after the injection.

Figure 15:
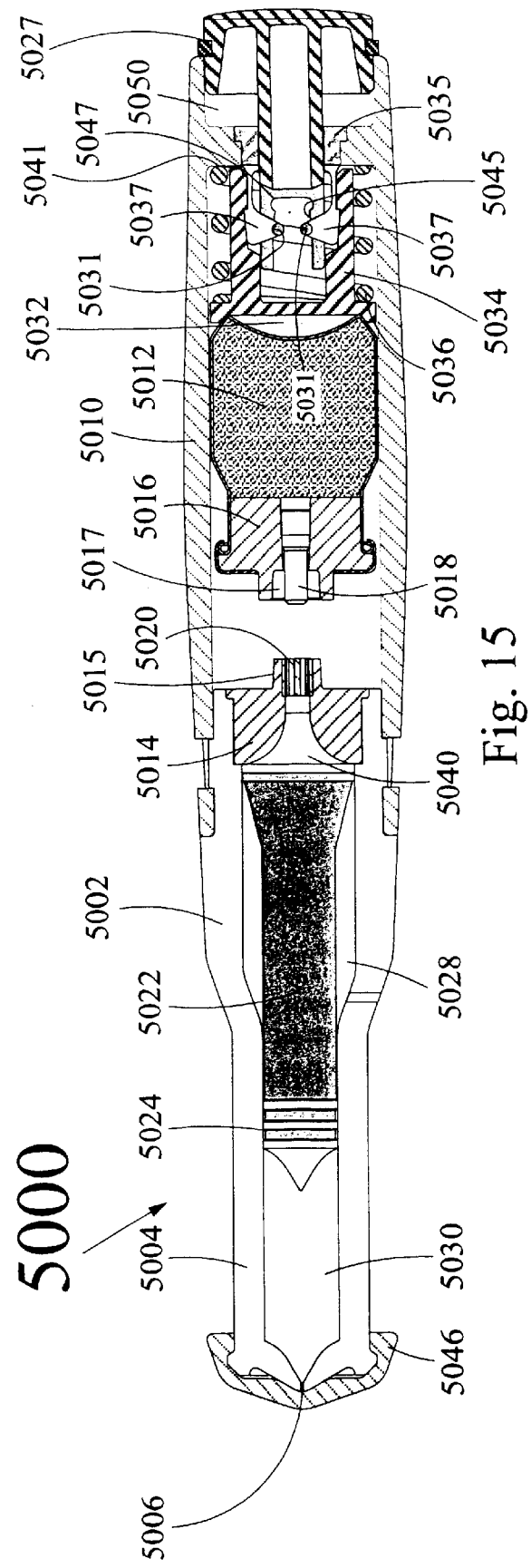
FIG. 15 is a cross-sectional diagram of the needle-less injector device with the gas power source as shown along the line 15—15 in FIG. 14 prior to an injection.
Figure 16:
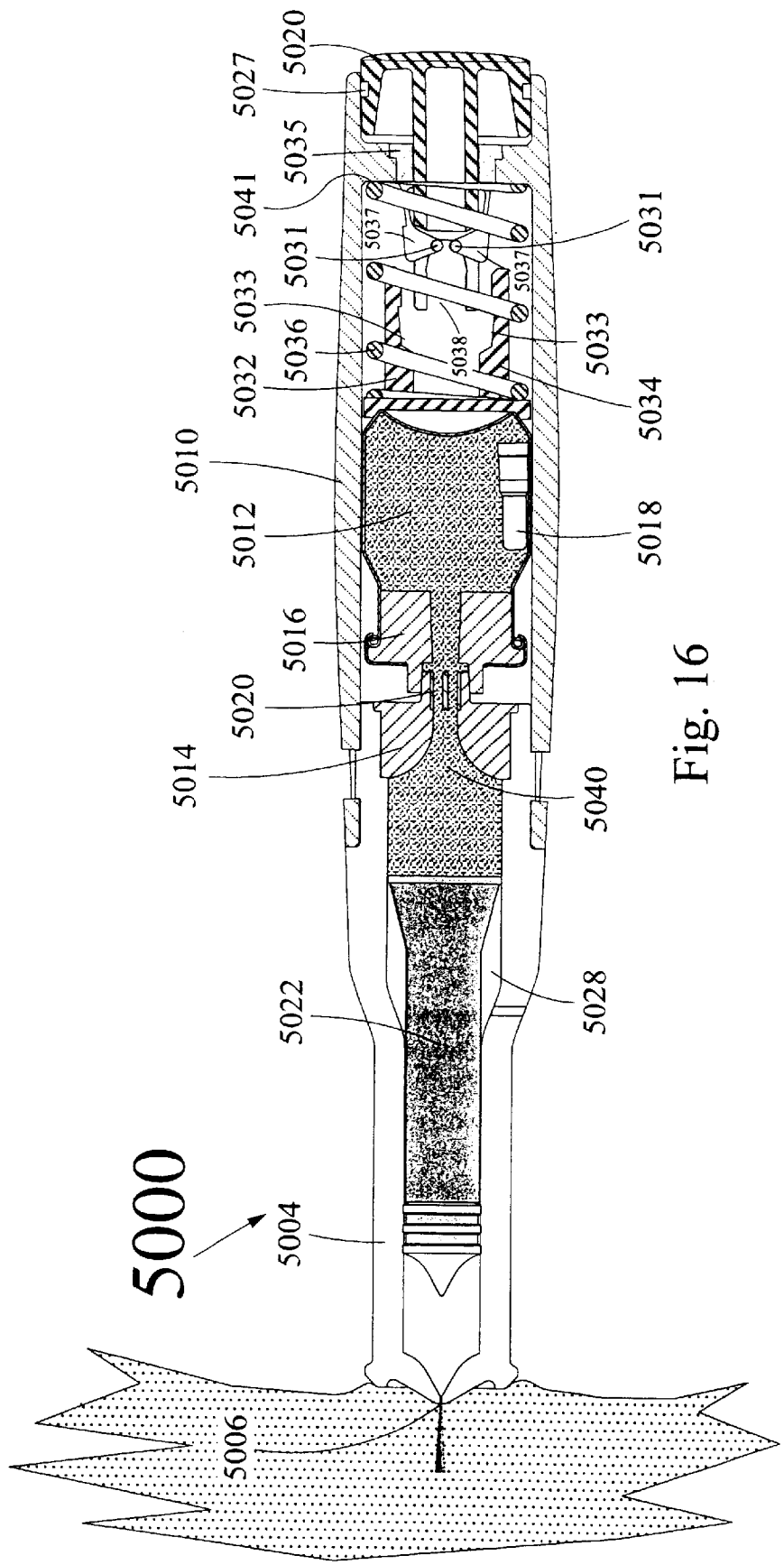
FIG. 16 is a cross-sectional diagram of the needle-less injector device with the gas power source after an injection.
Figure 17D:
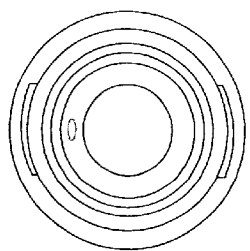
FIGS. 17a–d are various views of an ampoule and plunger housing in accordance with the fifth embodiment of the present invention.
Figure 17B:
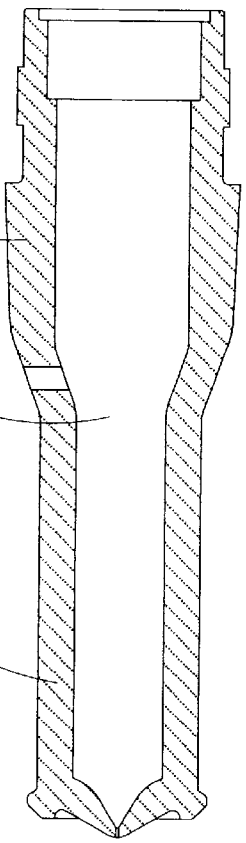
Figure 17A:
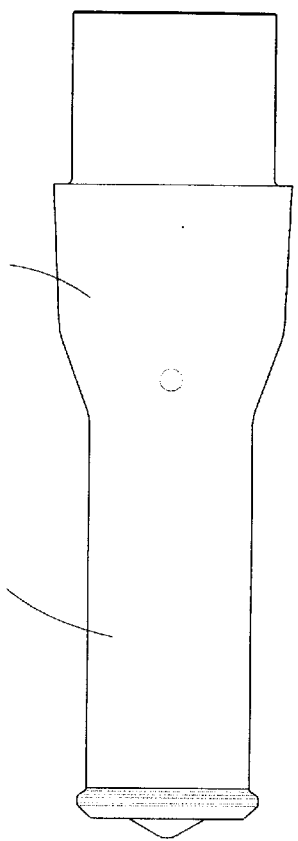
Figure 17C:
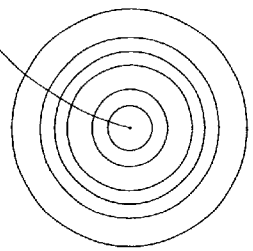
Figure 18A:
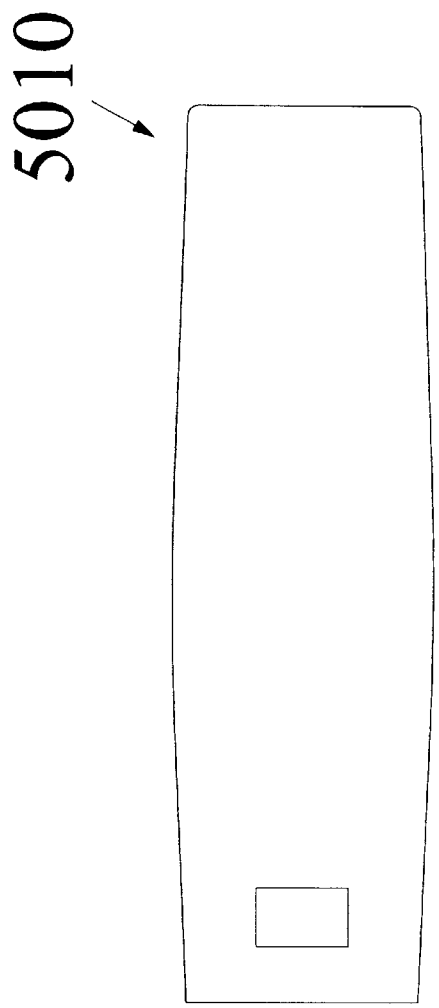
FIGS. 18a–d are various view of the actuator cap in accordance with the fifth embodiment of the present invention.
Figure 18B:
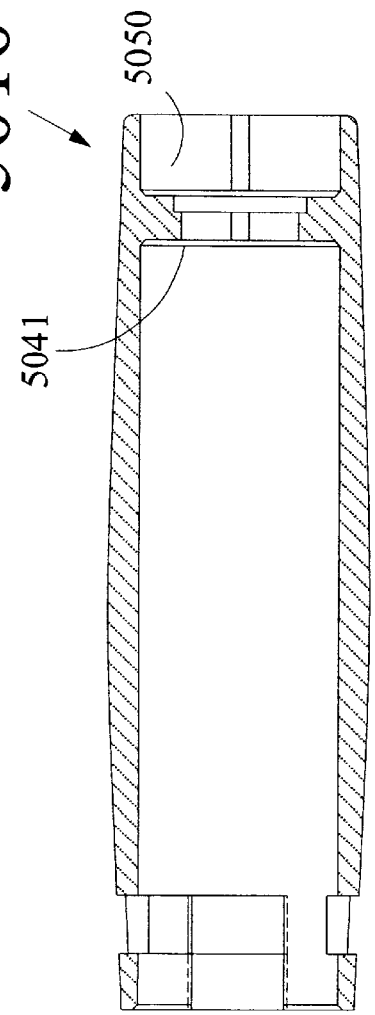
Figure 18D:
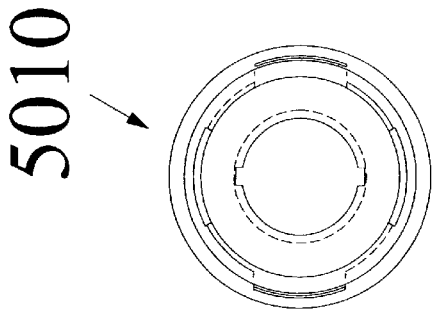
Figure 18C:
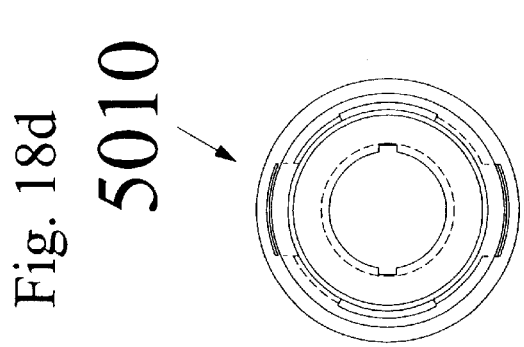
Figure 19D:
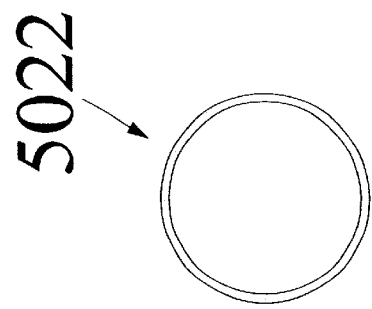
FIGS. 19a–d are various view of the plunger shaft in accordance with the fifth embodiment of the present invention.
Figure 19A:
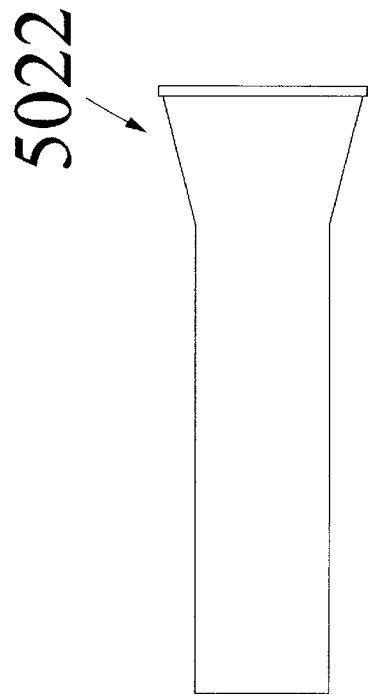
Figure 19C:
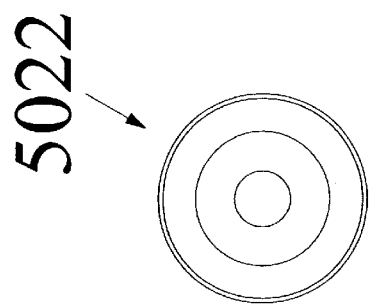
Figure 19B:
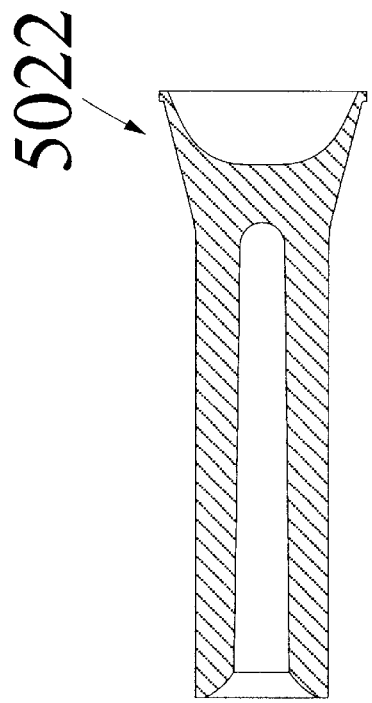
Figure 20D:
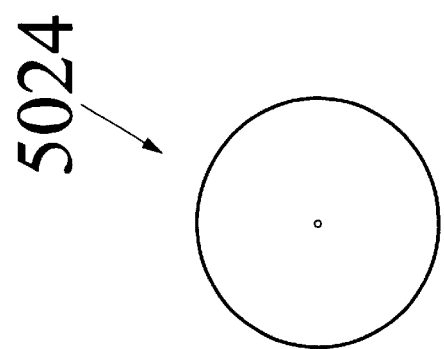
FIGS. 20a–d are various views of the plunger in accordance with the fifth embodiment of the present invention.
Figure 20A:
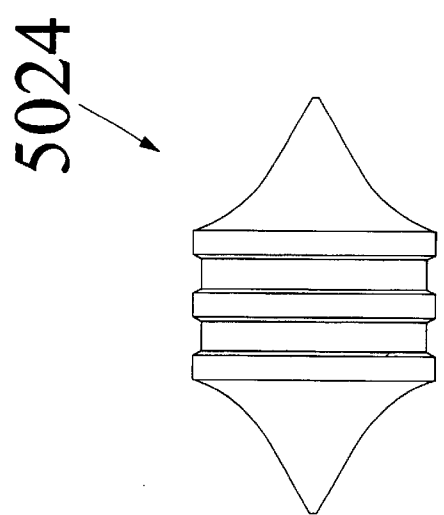
Figure 20B:
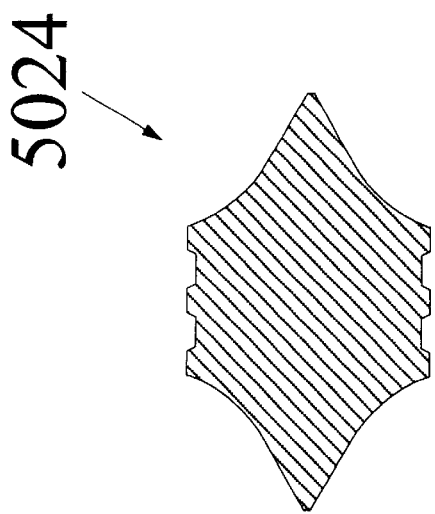
Figure 20C:
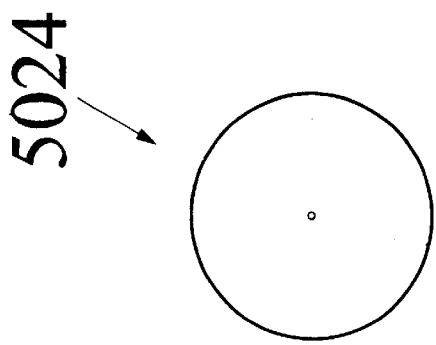
Figure 21A:
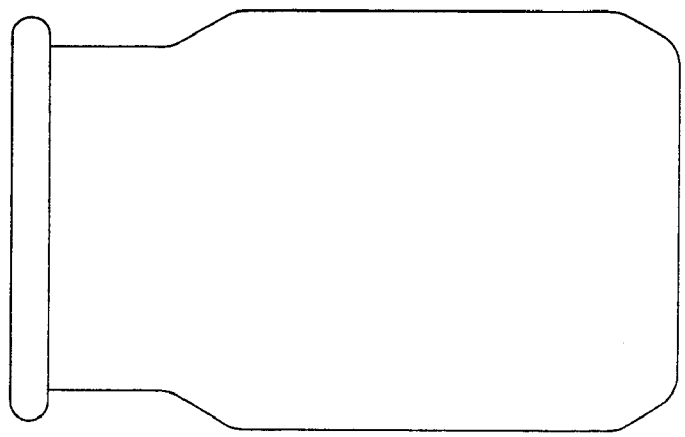
FIGS. 21a–b are various view of the gas capsule in accordance with the first embodiment of the present invention.
Figure 21B:
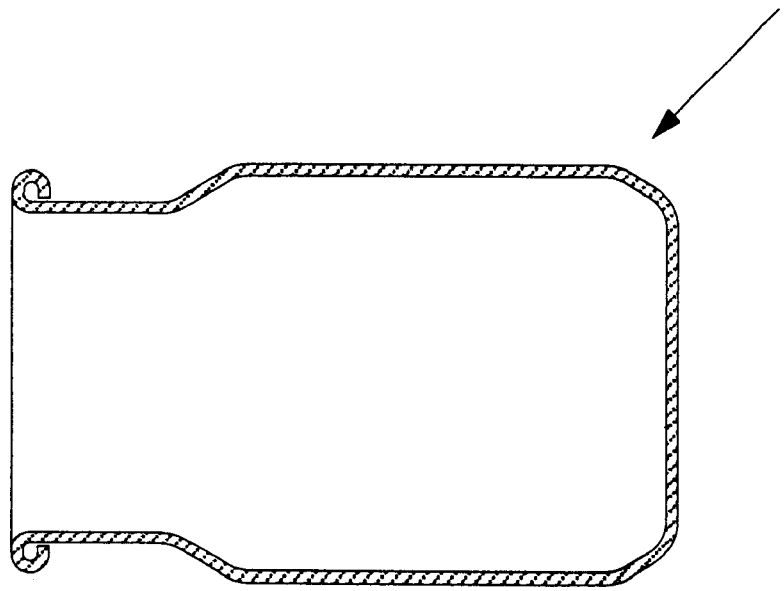
Figure 23D:
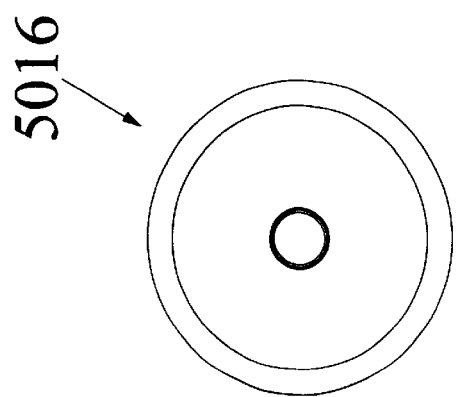
FIGS. 23a–d are various view of the barrel valve body in accordance with the fifth embodiment of the present invention.
Figure 23B:
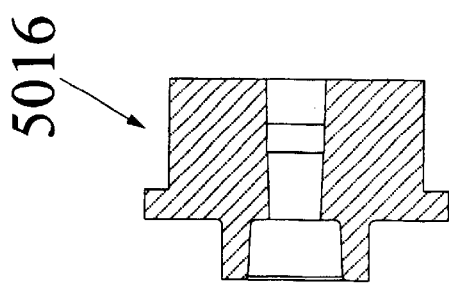
Figure 23A:
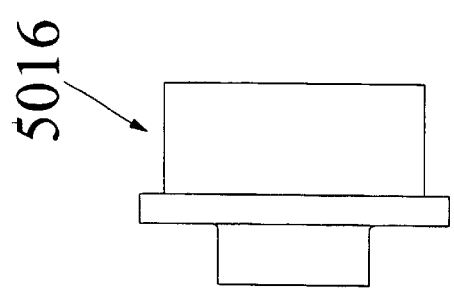
Figure 23C:
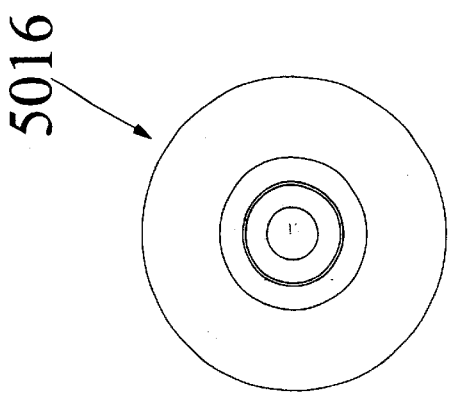
Figure 24A:
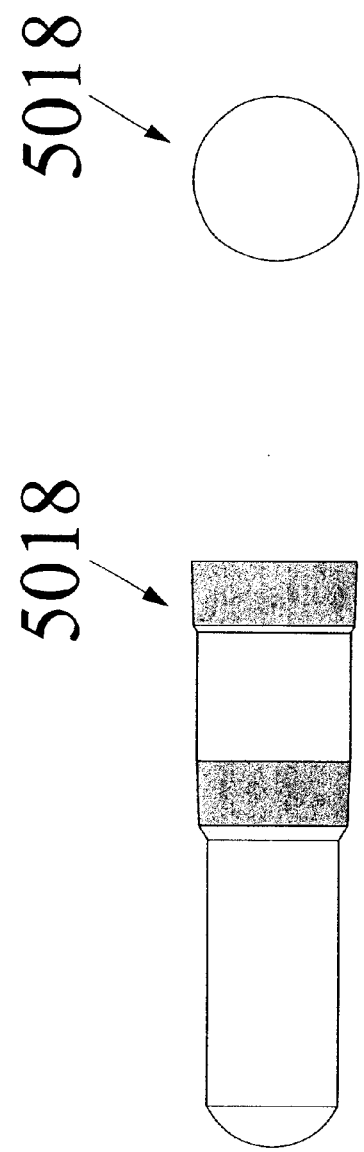
FIGS. 24a–d are various view of the slideable barrel valve in accordance with the fifth embodiment of the present invention.
Figure 24B:
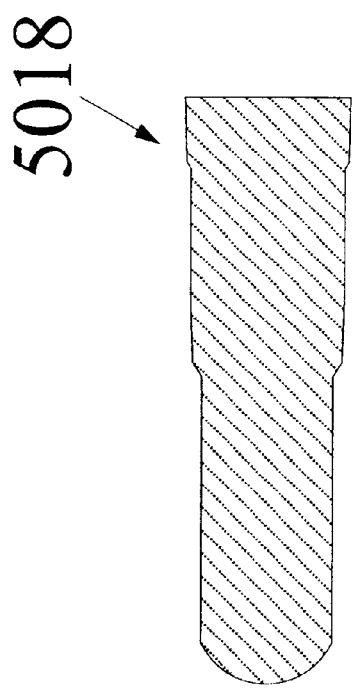
Figure 24C:
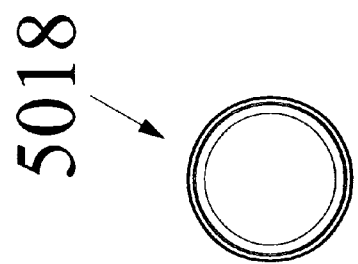
Figure 24D:
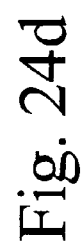
Figure 27A:
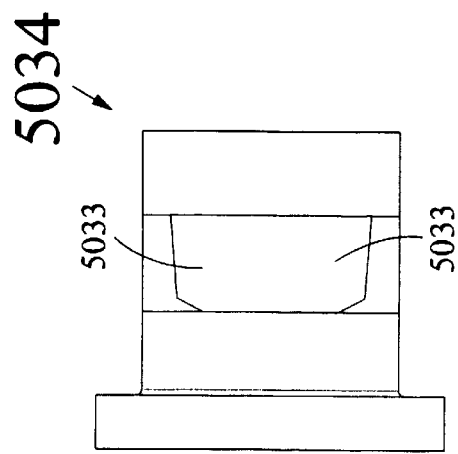
FIGS. 27a–h are various view of the spring tensioner in accordance with the fifth embodiment of the present invention.
Figure 27B:
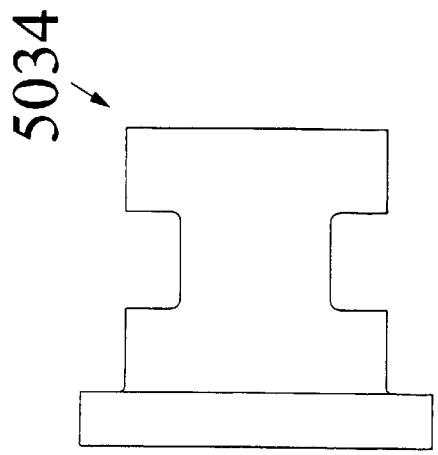
Figure 27E:
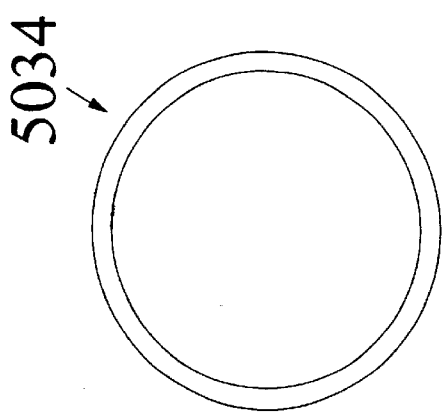
Figure 27F:
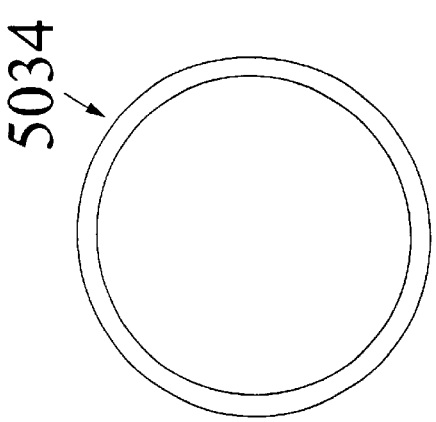
Figure 27C:
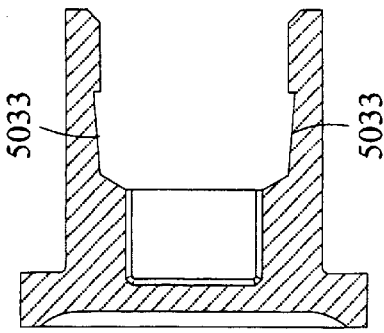
Figure 27D:
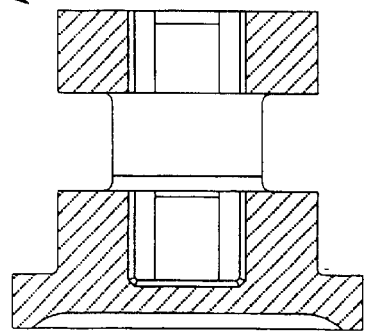
Figure 27G:
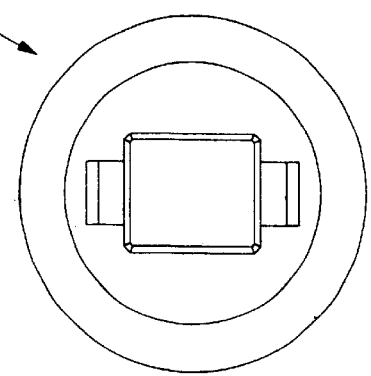
Figure 27H:
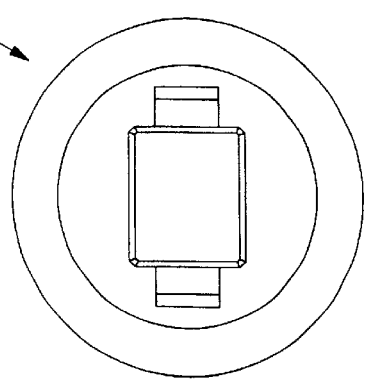

Depression of the actuator button 5029 releases the spring retainer 5034 so that the spring 5036 moves the gas charge 5012 towards the ampoule 5004 and the slide valve hub 5014 (from the positions of FIG. 15 to FIG. 16). The slide valve hub 2014 includes a gas distributor (or channel) 5040 formed in the slide valve hub 5014 to act a conduit to direct the expelled gas from the gas diffuser sleeve 5020 and to act on the plunger shaft 5022. The gas diffuser sleeve 5020 and the slideable valve hub 5014 press against the tapered slideable barrel valve 5018 to unseat it from the barrel valve body 5016 and cause it to penetrate (or intrude) into the interior of the gas charge 5012 to open the gas channel 5042 in the barrel valve body 5016 to let the gas from the gas charge 5012 escape. The diameter of the gas charge 5012 and the barrel valve body 5016 are selected so that the parts will slide freely within the interior of the actuator cap 5010 and to prevent misalignments and shifting during transport and activation. In alternative embodiments, guides, tracks, slots, or the like may be used. Generally, the slideable barrel valve 5018 will remain loose inside the gas charge 5012 and is prevented from reseating by the slide valve hub 5014 and the gas diffuser sleeve 5020.

In preferred embodiments, the slideable barrel valve 5018 is made from plastic, metal, ceramic, glass, or the like, and is coated by a dry lubricant that provides an air tight seal as the tapered shape is pressed down by the gas pressure in the gas charge 5015. However, the dry lubricant permits the slideable barrel valve 5018 to be unseated by the slide valve hub 5014. In alternative embodiments, the slideable barrel valve 5018 is formed from the same material as the barrel valve body 5016. The slideable barrel valve 5018 may also be augmented with an o-ring, or other type of seal instead of, or in addition, to the dry lubricant. In further alternative embodiments, the slideable barrel valve 5018 is retained in the barrel valve body 5016 by a detente, snap fit, friction or the like that maintains the position of the slideable barrel valve 5018 until the gas charge 5012 develops sufficient gas pressure to press the tapered slideable barrel valve 5018 into the barrel valve body 5016 to seal off the opening in the barrel valve body 5016.

In preferred embodiments, the gas contained in the gas charge 5012 is CO2. However, alternative embodiments, may use other gas, such as air, nitrogen, noble gases, mixtures, liquid/gas combinations, or the like. In preferred embodiment, the main housing 5002, actuator cap 5010, plunger shaft 5022, gas diffuser sleeve 5020, and actuator button 5029 are made of polycarbonate, or other suitable materials, such as plastic, metal, composites, ceramics or the like. The slide valve hub 5014 and container of the gas charge 5012 are formed from metal. However, other materials, such as plastic, glass, composites, laminates, ceramics, glass, or the like, may be used. Preferably, the plunger 5024 is formed of an elastomeric material, such as rubber or plastic, or the like. Also, the plunger 5024 is preferably shaped to fit within a matched recess in the end of the plunger shaft 5022 to minimize twisting or jamming during activation, and matches the shape of the orifice 5006 to minimize left over fluid at the end of an injection and to maintain the velocity of the escaping fluid throughout the injection.

In addition, a protective cap 5046 that covers the orifice 5006 of the ampoule can be a hard material, such as plastic, metal or the like, or a soft generally compliant rubber material. The protective cap 5046 is generally snapped onto the end of the ampoule 5004. However, alternative embodiments may utilize threads. Further, the safety clip 5026 can be a hard material, such as plastic, metal or the like, or a soft generally compliant rubber material, if it can resist movement of the actuator button 5029 towards the ampoule 5004.

To use the needle-less injector device 5000, the user removes the protective cap 5046 that covers the orifice 5006 of the ampoule 5004. The user also removes the safety clip 5026. Next, the user places the orifice 5006 and end of the ampoule 5004 against the tissue (such as skin, organs, different skin layers or the like) so that the needle-less injector is generally perpendicular to the tissue, as described above. The user grasps the sides of the actuator cap 5010 and then presses on the actuator button 5029 to move it towards the ampoule 5004. As the actuator button 5029 moves along the actuator cap 5010, the lock teeth 5037 of the spring tensioner 5035 are withdrawn by the sear base structure 5031 from the recess 5033 of the spring retainer 5034 to release the spring retainer 5034. The spring 5036 then moves the gas charge 5012, barrel valve body 5016 and spring retainer 5034 towards the gas diffuser sleeve 5020 and the slide valve body 5014, which eventually displaces the slideable barrel valve 5018 to penetrate (or intrude into) the gas charge 5012 and release the gas in the gas charge 5012. As the gas is released from the gas charge 5012, the spring retainer 5034 and spring 5036 resist rearward movement of the gas charge 5012. Preferably, the gas charge includes sufficient gas to provide sufficient pressure regardless of the position of the gas charge 5012 after the slideable barrel valve 5018 has been displaced by the gas diffuser sleeve 5020 and the slide valve hub 5014. The gas then flows through the gas diffuser sleeve 5020 and down the gas bore 5040 in the slide valve hub 5014 and presses against the plunger shaft 5022. As the released gas escapes, the pressure quickly increases to drive the plunger shaft 5022 forward, which in turn drives the plunger 5024 forward towards the orifice 5006 in the ampoule 5004. As the plunger 5024 travels forward, fluid is expelled out of the orifice 5006 to pierce the tissue and deliver the fluid below the surface of the tissue.

Figure 29:
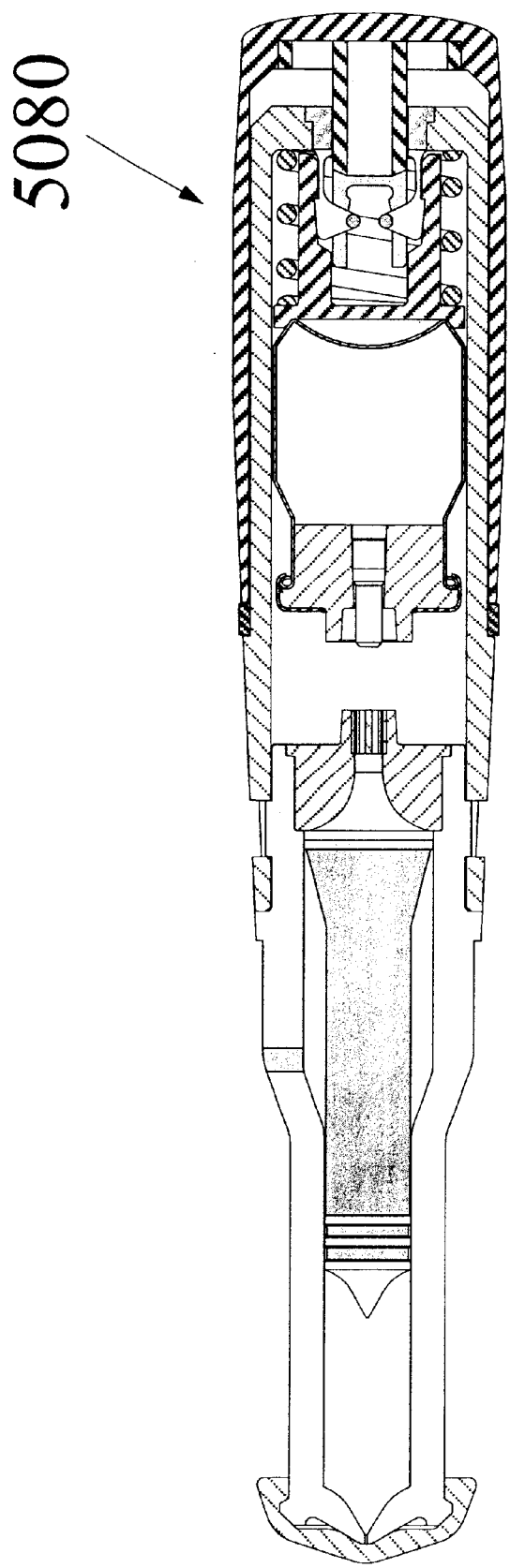
FIG. 29 is a cross-sectional view of a needle-less injector in accordance with the fifth embodiment of the present invention with a variation on the actuator button.

In alternative embodiments, the actuator cap 5010 may include a spring (not shown) in area 5050 between the actuator cap 5010 and the actuator button 5029 to resist depression of the actuator button 5029. In preferred embodiments, a metal spring, made of music wire or the like, with a loaded force of 2.2 lbs/in2 may be used. However, in alternative embodiments, other elastic or expansive materials, such as foam rubber, leaf springs, gas pillows or the like may be used in place of the spring or different spring tensions may be used. This would permit the actuator button 5029 to require a certain pressure to be exerted prior to activation, as opposed to the simple friction present between the actuator shaft 5039 and lock teeth 5037 of the actuator cap 5010. In further embodiments, the top of the actuator button 5029 may be formed as a cap structure 5080 (see FIG. 29) that slides over and covers the sides of the actuator cap 5010. The safety clip 5026 would then be attached to the actuator cap 5010 in a position to prevent premature depression of the actuator button/cap structure. An advantage of this actuator button/cap structure 5080 is that the user grasps the side of the actuator button/cap structure 5080 and resistance of the skin (or tissue) as discussed above is used as part of the triggering process.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A needle-less injector suitable for injecting fluid through a skin surface of a patient, the needle-less injector comprising:
    a housing containing the fluid and a sealed gas storage chamber containing a gas;
    a driver that forces the fluid out of the housing at a sufficient speed to pierce the skin surface of the patient;
    an intruding gas chamber activating mechanism is mounted in the housing to intrude through the sealed gas chamber to release the gas into the housing;
    a resistance sensitive trigger operatively coupled to the intruding gas chamber activating mechanism to release the gas from the gas chamber into the housing to activate the driver to force the fluid out of the housing upon application of a predetermined amount of pressure to the resistance sensitive trigger that is opposed by a predetermined amount of resistance from the skin surface of the patient resulting from the housing having contact with the skin surface of the patient, such that the fluid is forced out of the housing by the driver to pierce the skin surface of the patient.

2. The needle-less injector in accordance with claim 1, wherein the intruding gas chamber activating mechanism includes a valve member that is displaced and intrudes into the sealed gas chamber to release the gas from the gas chamber.

3. The needle-less injector in accordance with claim 1, further including a face on the housing for contacting the skin surface of the patient and aligning an orientation of the housing to produce the predetermined amount of resistance to allow for activation of the resistance sensitive trigger.

4. The needle-less injector in accordance with claim 1, wherein the resistance sensitive trigger is coupled to the housing to permit axial movement of the resistance sensitive trigger along the housing, wherein relative sizes of the housing and the resistance sensitive trigger permit activation of the resistance sensitive trigger when the housing is aligned between 0 and 15 degrees off an axis perpendicular to the skin surface of the patient.

5. The needle-less injector in accordance with claim 1, wherein the resistance sensitive trigger is positioned to be between the skin surface of the patient and an activating appendage of a user when activating the driver to force the fluid out of the housing.

6. The needle-less injector in accordance with claim 1, wherein the resistance sensitive trigger includes a resistance element that activates at a lower amount of pressure than the predetermined amount of resistance offered by the skin surface of the patient.

7. The needle-less injector in accordance with claim 6, wherein the resistance sensitive trigger includes a cap slidably attached to the housing and wherein the resistance element includes a spring coupled between the housing and the cap, wherein upon application of the predetermined amount of pressure to the cap of the resistance sensitive trigger the spring compresses, when the opposing resistance from the skin surface of the patient reaches the predetermined amount of resistance, to activate the driver to force the fluid out of the housing to pierce the skin surface of the patient.

8. A needle-less injector suitable for injecting fluid through a skin surface of a patient, the needle-less injector comprising:
    a housing containing the fluid and a sealed gas storage chamber containing a gas;
    a driver that forces the fluid out of the housing at a sufficient speed to pierce the skin surface of the patient;
    a gas chamber penetrating mechanism mounted in the housing to penetrate through the sealed gas chamber to release the gas into the housing;
    a resistance sensitive trigger operatively coupled to the gas chamber penetrating mechanism to release the gas from the gas chamber into the housing to activate the driver to force the fluid out of the housing upon application of a predetermined amount of pressure to the resistance sensitive trigger that is opposed by a predetermined amount of resistance from the skin surface of the patient resulting from the housing having contact with the skin surface of the patient, such that the fluid is forced out of the housing by the driver to pierce the skin surface of the patient.

9. The needle-less injector in accordance with claim 8, wherein the gas chamber penetrating mechanism includes a valve member that is displaced and penetrates the sealed gas chamber to release the gas from the gas chamber.

10. The needle-less injector in accordance with claim 8, further including a face on the housing for contacting the skin surface of the patient and aligning an orientation of the housing to produce the predetermined amount of resistance to allow for activation of the resistance sensitive trigger.

11. The needle-less injector in accordance with claim 8, wherein the resistance sensitive trigger is coupled to the housing to permit axial movement of the resistance sensitive trigger along the housing, wherein relative sizes of the housing and the resistance sensitive trigger permit activation of the resistance sensitive trigger when the housing is aligned between 0 and 15 degrees off an axis perpendicular to the skin surface of the patient.

12. The needle-less injector in accordance with claim 8, wherein the resistance sensitive trigger is positioned to be between the s kin surface of the patient and an activating appendage of a user when activating the driver to force the fluid out of the housing.

13. The needle-less injector in accordance with claim 8, wherein the resistance sensitive trigger includes a resistance element that activates at a lower amount of pressure than the predetermined amount of resistance offered by the skin surface of the patient.

14. The needle-less injector in accordance with claim 13, wherein the resistance sensitive trigger includes a cap slidably attached to the housing and wherein the resistance element includes a spring coupled between the housing and the cap, wherein upon application of the predetermined amount of pressure to the cap of the resistance sensitive trigger the spring compresses, when the opposing resistance from the skin surface of the patient reaches the predetermined amount of resistance, to activate the driver to force the fluid out of the housing to pierce the skin surface of the patient.

15. A needle-less injector suitable for injecting fluid through a skin surface of a patient, the needle-less injector comprising:

a housing containing the fluid and a sealed gas storage chamber containing a gas, wherein the housing also contains an orifice;

a driver that forces the fluid out of the orifice of the housing at a sufficient speed to pierce the skin surface of the patient;

an intruding gas chamber activating mechanism mounted in the housing to intrude through the sealed gas chamber to release the gas into the housing;

a trigger operatively coupled to the intruding gas chamber activating mechanism to release the gas from the gas chamber into the housing to activate the driver to force the fluid out of the orifice of the housing by moving the trigger toward the orifice, such that the fluid is forced out of the orifice of the housing by the driver to pierce the skin surface of the patient.

16. The needle-less injector in accordance with claim 15, wherein the intruding gas chamber activating mechanism includes a valve member that is displaced and intrudes into the sealed gas chamber to release the gas from the gas chamber.

17. The needle-less injector in accordance with claim 15, wherein the trigger is activated upon application of a predetermined amount of pressure to the trigger that is opposed by a predetermined amount of resistance from the skin surface of the patient resulting from the housing having contact with the skin surface of the patient.

18. The needle-less injector in accordance with claim 15, further including a face on the housing for contacting the skin surface of the patient and aligning an orientation of the housing.

19. The needle-less injector in accordance with claim 15, wherein the trigger is coupled to the housing to permit axial movement of the trigger along the housing, wherein relative sizes of the housing and the trigger permit activation of the trigger when the housing is aligned between 0 and 15 degrees off an axis perpendicular to the skin surface of the patient.

20. The needle-less injector in accordance with claim 15, wherein the trigger is positioned to be between the skin surface of the patient and an activating appendage of a user when activating the driver to force the fluid out of the orifice of the housing.

21. The needle-less injector in accordance with claim 17, wherein the trigger includes a resistance element that activates at a lower amount of pressure than the predetermined amount of resistance offered by the skin surface of the patient.

22. The needle-less injector in accordance with claim 21, wherein the trigger includes at least one actuator slidably attached to the housing and wherein the resistance element includes a spring coupled between the housing and the at least one actuator, wherein upon application of the predetermined amount of pressure to the at least one actuator of the trigger the spring compresses, when the opposing resistance from the skin surface of the patient reaches the predetermined amount of resistance, to activate the driver to force the fluid out of the orifice of the housing to pierce the skin surface of the patient.

23. A needle-less injector suitable for injecting fluid through a skin surface of a patient, the needle-less injector comprising:

a housing containing the fluid and a sealed gas storage chamber containing a gas, and wherein the housing includes an orifice;

a driver that forces the fluid out of the orifice of the housing at a sufficient speed to pierce the skin surface of the patient;

a gas chamber penetrating mechanism mounted in the housing to penetrate through the sealed gas chamber to release the gas into the housing;

a trigger operatively coupled to the gas chamber penetrating mechanism to release the gas from the gas chamber into the housing to activate the driver to force the fluid out of the orifice of the housing by moving the trigger towards the orifice, such that the fluid is forced out of the orifice of the housing by the driver to pierce the skin surface of the patient.

24. The needle-less injector in accordance with claim 23, wherein the gas chamber penetrating mechanism includes a valve member that is displaced and penetrates the sealed gas chamber to release the gas from the gas chamber.

25. The needle-less injector in accordance with claim 23, wherein the driver is activated upon application of a predetermined amount of pressure to the trigger that is opposed by a predetermined amount of resistance from the skin surface of the patient resulting from the housing having contact with the skin surface of the patient.

26. The needle-less injector in accordance with claim 23, further including a face on the housing for contacting the skin surface of the patient and aligning an orientation of the housing.

27. The needle-less injector in accordance with claim 23, wherein the trigger is coupled to the housing to permit axial movement of the trigger along the housing, wherein relative sizes of the housing and the trigger permit activation of the trigger when the housing is aligned between 0 and 15 degrees off an axis perpendicular to the skin surface of the patient.

28. The needle-less injector in accordance with claim 23, wherein the trigger is positioned to be between the skin surface of the patient and an activating appendage of a user when activating the driver to force the fluid out of the orifice of the housing.

29. The needle-less injector in accordance with claim 25, wherein the trigger includes a resistance element that activates at a lower amount of pressure than the predetermined amount of resistance offered by the skin surface of the patient.

30. The needle-less injector in accordance with claim 27, wherein the trigger includes at least one actuator slidably attached to the housing and wherein the resistance element includes a spring coupled between the housing and the at least one actuator, wherein upon application of the predetermined amount of pressure to the at least one actuator of the trigger the spring compresses, when the opposing resistance from the skin surface of the patient reaches the predetermined amount of resistance, to activate the driver to force the fluid out of the orifice of the housing to pierce the skin surface of the patient.

* * * * *